US006228621B1

(12) United States Patent
Williams et al.

(10) Patent No.: US 6,228,621 B1
(45) Date of Patent: May 8, 2001

(54) PLASMIDS ENCODING IMMUNOGENIC PROTEINS AND INTRACELLULAR TARGETING SEQUENCES

(75) Inventors: William V. Williams, Havertown; Michael Madaio, Bryn Mawr; David B. Weiner, Merion Station, all of PA (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 08/957,001

(22) Filed: Oct. 23, 1997

Related U.S. Application Data

(60) Provisional application No. 60/029,592, filed on Oct. 23, 1996.

(51) Int. Cl.[7] .......................... C12P 21/04; A61K 39/00; A01N 43/04; C07K 1/00
(52) U.S. Cl. ................. 435/69.7; 424/185.1; 424/192.1; 514/44; 530/350; 536/23.4; 536/23.5
(58) Field of Search ...................... 435/69.7; 424/185.1, 424/192.1; 514/44; 530/350; 536/23.4, 23.5

(56) References Cited

U.S. PATENT DOCUMENTS

| | | | |
|---|---|---|---|
| 4,945,050 | 7/1990 | Sanford et al. | 435/172.1 |
| 5,036,006 | 7/1991 | Sanford et al. | 435/170.1 |
| 5,589,466 | 12/1996 | Felgner et al. | 514/44 |
| 5,593,972 | 1/1997 | Weiner et al. | 514/44 |
| 5,633,234 | * 5/1997 | August et al. | 514/44 |

FOREIGN PATENT DOCUMENTS

| | | |
|---|---|---|
| WO 90/11092 | 10/1990 | (WO) . |
| WO 93/17706 | 9/1993 | (WO) . |
| WO 94/02610 | 2/1994 | (WO) . |
| WO 94/04557 | 3/1994 | (WO) . |
| WO 94/16737 | 8/1994 | (WO) . |
| WO 95/24915 | 9/1995 | (WO) . |
| WO 95/26718 | 10/1995 | (WO) . |

OTHER PUBLICATIONS

Johansen, et al., C–Terminal KDEL–Modified Cystatin C is Retained in Transfected CHO Cells, Biochem Biophys. Res. Commun., vol. 172, No. 3, pp 1384–1391, see Fig. 2, pp. 1385, 1387, 1389 and 1390, Nov. 1990.*

Biocca, S., et al., "Expression and targeting of intracellular antibodies in mammalian cells", *EMBO J.*, 1990, 9, 101–108.

Chaudhary, V.K., et al., "A rapid method of cloning functional variable –region antibody genes in *Escherichia coli* as single–chain immunotoxins", *Proc. Natl. Acad. Sci. USA*, 1990, 87, 1066–1070.

Fynan, E.F., et al., "DNA Vaccines: A Novel Approach to Immunization", *Int. J. Immunopharmac.*, 1995, 17(2), 79–83.

Howell, M.D., et al., "Limited T–cell receptor β–chain heterogeneity among interleukin 2 receptor–positive synovial T cells suggests a role for superantigen in rheeumatoid arthritis", *Proc. Natl. Acad. Sci. USA*, 1991, 88, 10921–10925.

Jackson, M.R. et al., "Identification of a consensus motif for retention of transmembrane proteins in the endoplasmic reticulum", *EMBO J.*, 1990, 9, 3153–3162.

(List continued on next page.)

*Primary Examiner*—Hankyel Park
(74) *Attorney, Agent, or Firm*—Woodcock Washburn Kurtz Mackiewicz & Norris LLP

(57) ABSTRACT

Improved vaccines are disclosed. The improved vaccines include a nucleotide sequence that encodes a coding sequence that comprises an immunogenic target protein linked to or comprising an intracellular cellular targeting sequence, the coding sequence being operably linked to regulatory elements are disclosed. Methods of immunizing individuals are disclosed.

40 Claims, 14 Drawing Sheets

FACS Analysis of H221 Binding

OTHER PUBLICATIONS

Jackson, M.R. et al., "Retreival of Transmembrane Proteins to the Endoplasmic Reticulum", *J. Cell. Biol.,* 1993, 121(2), 317–333.

Kabat, et al. 1987, Sequence of Protein of Immunol. Interest, U.S. Dept. Of Health and Human Services, Bethesda, MD.

Letourneur, F. et al., "A Novel Di–Leucine Motif and a Tyrosine–Based Motif Independently Mediate Lysosmoal Targeting and Endocytosis of CD3 Chains", *Cell,* 1992, 69, 1143–1157.

Madaio, M.P. et al., "Responsiveness of Autoimmune and Normal Mice to Nucleic Acid Antigens", *J. Immunol.,* 1984, 132, 872–876.

McDonnell, W.M. et al., "Molecular Midicine: DNA Vaccines", *New Engl. J. Med.,* 1996, 334(1), 42–45.

Nilsson, T. et al., "Short Cytoplasmic Sequences Serve as Retention Signals for Transmembrane Proteins in the Endoplasmic Reticulum", *Cell,* 1989, 58, 707–718.

Oksenberg, J.R., et al., "Limited heterogeneity of rearranged T–cell receptor Vα transcripts in brains of mutiple sclerosis patients", *Nature,* 1990, 345, 344–346.

Paliard, X., et al., "Evidence for the Effects of a Superantigen in Rheumatoid Arthritis", *Science,* 1991, 253, 325–329.

Pardoll, D.M. et al., "Exposing the Immunology of Naked DNA Vaccines", *Immunity,* 1995, 3, 165–169.

Robinson, A., "DNA–Based Vaccines: New Possibilities for Disease Prevention and Treatment", *Can. Med. Assoc. J.,* 1995, 152(10), 1629–1632.

Spooner, R.A. et al., "DNA vaccination for cancer treatment", *Gene Therapy,* 1995, 2, 173–180.

Srikatan, V. et al., "Cloning and biological characterization of human single–chain Fv fragments that mediate neutralization of HIV–1", *AIDS,* 1994, 8, 1525–1532.

Syrengelas, A.D. et al., "DNA immunization induces protective immunity against B–cell lymphoma", *Nature Medicine,* 1996, 2, 1038–1041.

Vlahakos, D.V. et al., "Anti–DNA antibodies form immune deposits at distinct glomerular and vascular sites", *Kidney Int.,* 1992, 41, 1690–1700.

Waisman, A. et al., "Suppressive vaccination with DNA encoding a variable region gene of the T–cell receptor prevents autoimmune encephalomyelitis and activates Th2 immunity", *Nature Medicine,* 1996, 2, 899–905.

Wang, B. et al., "Gene inoculation generates immune responses against human immunodeficiency virus type 1", *Proc. Natl. Acad. Sci. USA,* 1993, 90, 4156–4160.

Williams, W. V. et al., "Restricted Heterogeneity of T Cell Receptor Transcripts in Rheumatoid Synovium", *J. Clin. Invest.,* 1992, 90, 326–333.

Wucherpfennig, et al., "Shared Human T Cell Receptor $V_\beta$ Usage to Immunodominant Regions of Myelin Basic Protein", *Science,* 1990, 248, 1016–1019.

U.S. application No. 08/008,342, Weiner, et al., filed Jan. 26, 1993.

U.S. application No. 08/029,336, Weiner, et al., filed Mar. 11, 1993.

Andersson, M. et al., "Impaired Intracellular Transport of Class 1 MHC Antigens as a Possible Means for Adenoviruses to Evade Immune Surveillance", *Cell,* 1985, 43, 215–222.

* cited by examiner

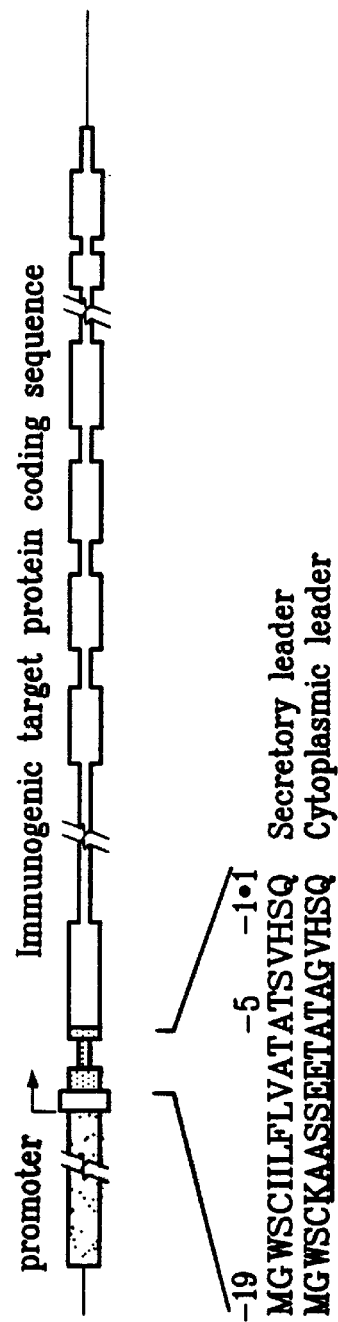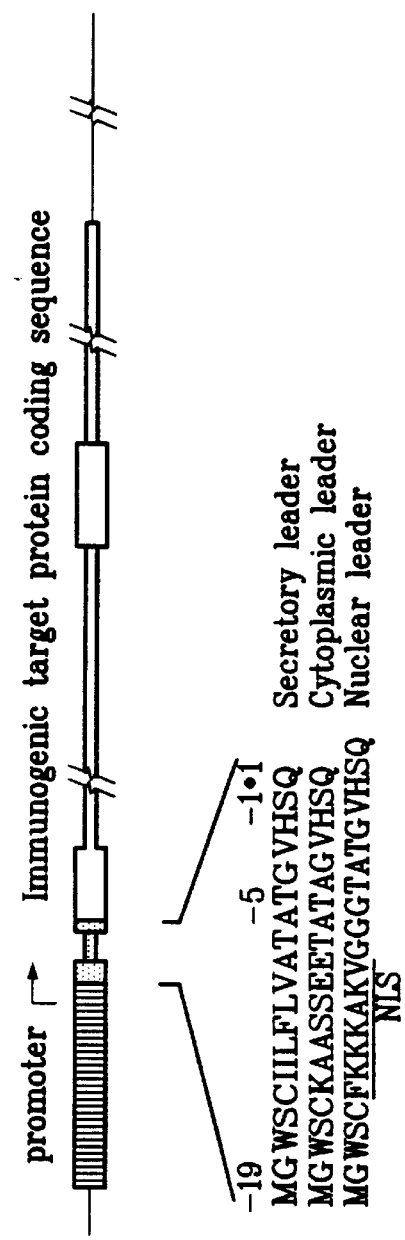
FIG. 6A
FIG. 6B

| | | | | | | | | | | | | | | | |
|---|---|---|---|---|---|---|---|---|---|---|---|---|---|---|---|
| 1 | Adenovirus E19 | K | Y | K | S | R | R | S | F | I | D | E | K | K | M P |
| 2 | UDPGT HP1 | - | - | - | - | - | V | K | K | A | S | K | S | K | T H |
| 3 | UDPGT H25 | - | - | - | - | - | R | T | G | K | K | G | K | R | D |
| 4 | UDPGT H4 | - | - | - | - | - | A | K | K | G | K | K | K | K | R D |
| 5 | 53KDa SER | - | - | - | - | - | E | T | P | K | N | R | Y | K | K H |
| 6 | HMG CoA | - | - | - | - | - | L | Q | G | A | C | T | K | K | T A |
| 7 | Signal pep 22/23K | - | - | - | - | - | P | D | T | Y | E | I | T | K | S Y |
| 8 | Ribophorin I | - | - | - | - | - | T | K | I | D | H | I | L | D | A L |
| 9 | Ribophorin II | - | - | - | - | - | A | Q | Q | A | V | K | R | T | A H |
| 10 | ERP99 | - | - | - | - | - | E | K | E | S | T | E | K | D | E L |
| 11 | CD8 | V | V | K | S | G | D | K | P | S | L | S | A | R | Y V |
| | | 1 | 2 | 3 | 4 | 5 | 6 | 7 | 8 | 9 | 10 | 11 | | | |

| | |
|---|---|
| Human Ad2 E19 | - K Y K S R R S F I D E K K M P |
| Human Ad5 E19 | - K Y K S R R S F I E E K K M P |
| Human Ad3 E19 | - V I R P R Q S N E E K E K M P |
| | |
| Human UDPGT H25 | - C V W K F Y R T G K K G K R D |
| Human UDPGT H4 | - C F R K L A K K G K K K K R D |
| Human UDPGT HP1 | - G K K G R V K K A H K S K T H |
| Rat UDPGT R38 | - I Y R L F V K K E K K M K N E |
| Rat UDPGT R23 | - M Y R F F V K K E K K M K N E |
| Rat UDPGT R1 | - V Y R F F V K K E K K T K N E |
| Rat UDPGT 2F | - F C C R K T A N M G K K K K E |
| Rat UDPGT K39 | - G G K G R V K K G H K S K T H |
| Mouse UDPGT | - I Y R F F V K K E N K M K N E |
| | |
| Human HMG CoA | - I N L Q D L Q G T C T K K S A |
| Hamster HMG CoA | - I N L Q D L Q G T C T K K S A |
| | |
| SER 53Kd | - D K T G C G T P K N R Y K K H |

Inserts and Targeting Strategy

PLASMIDS ENCODING IMMUNOGENIC PROTEINS AND INTRACELLULAR TARGETING SEQUENCES

CROSS REFERENCE TO RELATED APPLICATIONS

This application claims priority to Provisional Application Serial Number 60/029,592 filed on Oct. 23, 1996 which is incorporated herein by reference.

FIELD OF THE INVENTION

The present invention relates to improved protective and therapeutic vaccines and improved methods for prophylactically and/or therapeutically inducing immune responses against antigens.

BACKGROUND OF THE INVENTION

DNA vaccines represent an emerging field which provides the means to prevent and treat disorders, diseases, conditions and infections by inducing immune responses in individuals which are directed at antigens associated with such disorders, diseases, conditions and infections. Essentially, plasmid DNA that includes coding sequences for antigens operably linked to regulatory elements required for gene expression is administered to individuals. The cells of the individual take up the plasmid DNA and the coding sequence is expressed. The antigen so produced becomes a target against which an immune response is directed. The immune response directed against the antigen provided the prophylactic or therapeutic benefit to the individual against any allergen, pathogen, cancer cell or autoimmune cell that includes an epitope that is recognized by the immune response against the antigen.

DNA vaccines include naked and facilitated vaccines. Further, they may be administered by a variety of techniques including several different devices for administering substances to tissue. The published literature includes several review articles that describe aspects of DNA vaccine technology and cite some of the many reports of results obtained using the technology. The following review articles which are each incorporated herein by reference as are each of the references cited in each review article discuss DNA vaccine technology: McDonnel W. M. and F. K. Askari 1996 New Engl. J. Med. 334(1)42–45; Robinson, A. 1995 Can. Med. Assoc. J. 152(10):1629–1632; Fynan, E. F. et al. 1995 Int. J. Immunopharmac. 17(2)79–83; Pardoll, D. M. and A. M. Beckerleg 1995 Immunity 3:165–169; and Spooner et al. 1995 Gene Therapy 2:173–180.

While such vaccines are often effective to immunize individuals prophylactically or therapeutically against pathogen infection or human diseases, there is a need for improved vaccines. There is a need for compositions and methods which produce an enhanced immune response.

SUMMARY OF THE INVENTION

The present invention relates to a plasmid which comprises nucleotide sequences that encodes an immunogenic target antigen operably linked to regulatory elements necessary for expression in eukaryotic cells wherein the nucleotide sequence that encodes the immunogenic antigen includes a nucleotide sequence that encodes a signal sequence which directs trafficking of the immunogenic target antigen within the cell. In some preferred embodiments, the immunogenic target antigen is a pathogen antigen, a cancer-associated antigen or an antigen linked to cells associated with autoimmune diseases. In some embodiments, the nucleotide sequence that encodes a signal sequence which directs trafficking of the immunogenic target antigen within the cell encodes a signal sequence which directs the immunogenic target antigen to be secreted or to localize to the cytoplasm, the cell membrane, the endoplasmic reticulum, or a lysosome. In some embodiments, the nucleotide sequence that encodes a signal sequence which directs intracellular trafficking of the immunogenic target antigen is a non-native signal sequence.

The present invention relates to a method of inducing, in an individual, an immune response against an antigen comprising the step of administering to an individual, a plasmid which comprises a nucleotide sequence that encodes an immunogenic target antigen operably linked to regulatory elements necessary for expression in eukaryotic cells wherein the nucleotide sequence that encodes the immunogenic antigen includes a nucleotide sequence that encodes a signal sequence which directs trafficking of the immunogenic target antigen within the cell. In some preferred embodiments, the immunogenic target antigen is a pathogen antigen, a cancer-associated antigen or an antigen linked to cells associated with autoimmune diseases. In some embodiments, the nucleotide sequence that encodes a signal sequence which directs trafficking of the immunogenic target antigen within the cell encodes a signal sequence which directs the immunogenic target antigen to be secreted or to localize to the cytoplasm, the cell membrane, the endoplasmic reticulum, or a lysosome. In some embodiments, the nucleotide sequence that encodes a signal sequence which directs intracellular trafficking of the immunogenic target antigen is a non-native signal sequence.

The present invention relates to improved DNA vaccines which comprises nucleotide sequences that encodes an immunogenic target antigen operably linked to regulatory elements necessary for expression in eukaryotic cells wherein the nucleotide sequence that encodes the immunogenic antigen includes a nucleotide sequence that encodes a signal sequence which directs trafficking of the immunogenic target antigen within the cell. In some preferred embodiments, the immunogenic target antigen is a pathogen antigen, a cancer-associated antigen or an antigen linked to cells associated with autoimmune diseases. In some embodiments, the nucleotide sequence that encodes a signal sequence which directs trafficking of the immunogenic target antigen within the cell encodes a signal sequence which directs the immunogenic target antigen to be secreted or to localize to the cytoplasm, the cell membrane, the endoplasmic reticulum, or a lysosome. In some embodiments, the nucleotide sequence that encodes a signal sequence which directs intracellular trafficking of the immunogenic target antigen is a non-native signal sequence.

The present invention relates to a method of immunizing an individual against a pathogen, cancer or an autoimmune disease comprising the step of administering to an individual, a DNA vaccine which comprises a nucleotide sequence that encodes an immunogenic target antigen operably linked to regulatory elements necessary for expression in eukaryotic cells wherein the nucleotide sequence that encodes the immunogenic antigen includes a nucleotide sequence that encodes a signal sequence which directs trafficking of the immunogenic target antigen within the cell. In some preferred embodiments, the immunogenic target antigen is a pathogen antigen, a cancer-associated antigen or an antigen linked to cells associated with autoimmune diseases. In some embodiments, the nucleotide sequence that encodes a signal sequence which directs trafficking of the immunogenic target antigen within the cell encodes a signal sequence which directs the immunogenic target antigen to be secreted or to localize to the cytoplasm, the cell membrane, the endoplasmic reticulum, or a lysosome. In some embodiments, the nucleotide sequence that encodes a signal sequence which directs intracellular trafficking of the immunogenic target antigen is a non-native signal sequence.

BRIEF DESCRIPTION OF THE DRAWINGS

FIGS. 6A and 6B show genetic constructs of the invention that comprise specific leader sequences.

FIGS. 7A and 7B shows several C terminal sequences for ER retention.

FIG. 10A shows data from experiments in which the vaccines targeted the H221 $V_H$ or Fv region to the ER for secretion. FIG. 10B shows data from experiments in which the vaccines targeted the H221 $V_H$ or Fv region to the ER for retention. FIG. 10C shows data from experiments in which the vaccines targeted the H221 $V_H$ or Fv region to the cytosol.

DETAILED DESCRIPTION OF THE INVENTION

Figure 1:
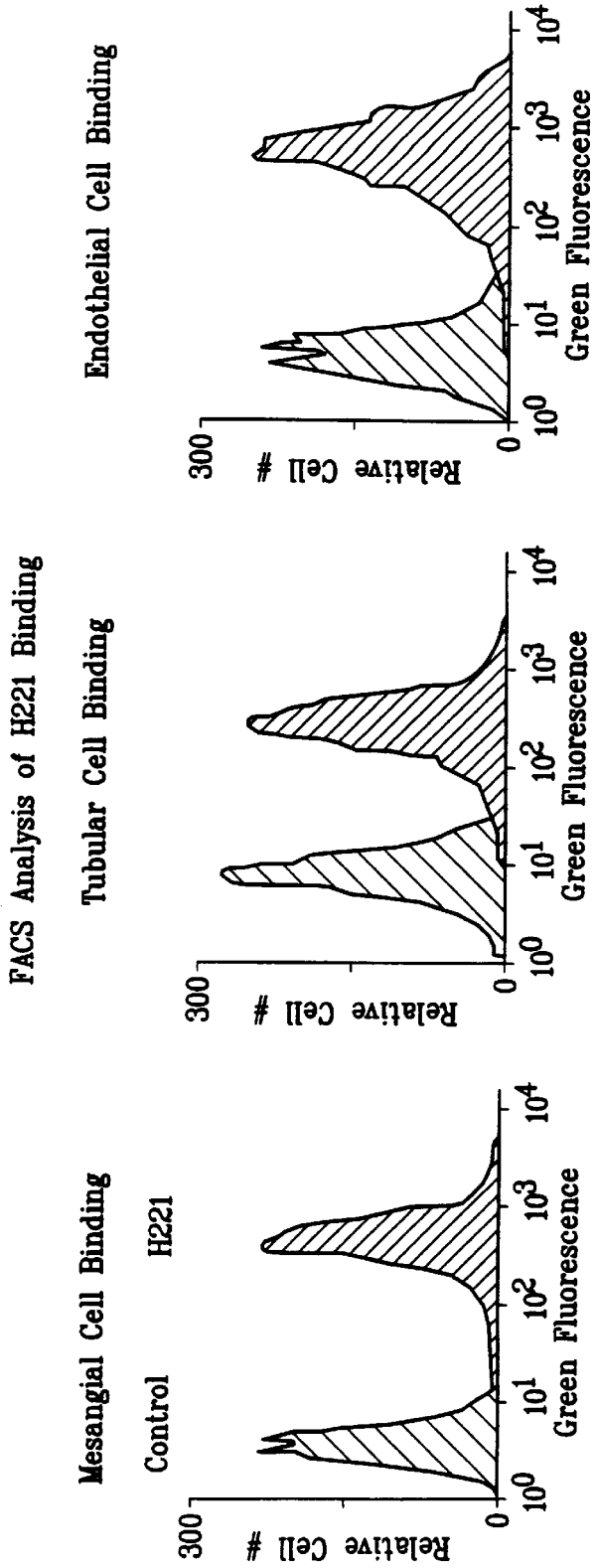
FIG. 1 shows data from FACS analysis of H221 binding.

The present invention relates to improved DNA vaccines. DNA vaccines are described in U.S. Pat. Nos. 5,589,466 and 5,973,972, and PCT published applications PCT/US90/01515, PCT/US93/02338, PCT/US93/048131, and PCT/US94/00899, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference. Further, the review articles cited above describe DNA vaccine technology and cite examples of DNA vaccines. In each case, plasmid DNA is delivered to cells of an individual which take up the plasmid and express immunogenic target proteins encoded by the plasmids. The immune response generated against the immunogenic target protein provides a prophylactic or therapeutic benefit to the vaccinated individual.

According to the present invention, the coding sequence on the plasmid that encodes the immunogenic target protein is provided with a coding sequence that encodes an amino acid sequence whose presence on the protein results in a specific intracellular localization of the expressed protein. The nucleotide sequences that encode amino acid sequences which direct intracellular protein trafficking and which are included in the coding sequences of immunogenic proteins that are included in plasmid constructs used as DNA vaccine compositions direct localization to specific areas in the cells which result in enhancement of specific immune responses.

As used herein, the term "genetic construct" is meant to refer to plasmids which comprise coding sequences that encode an immunogenic target protein and an amino acid sequence that directs intracellular protein trafficking, the coding sequences being operably linked to regulatory elements required for expression of the coding sequences in eukaryotic cells. Regulatory elements for DNA expression include a promoter and a polyadenylation signal. In addition, other elements, such as a Kozak region, may also be included in the genetic construct. Initiation and termination signals are required regulatory elements which are often considered part of the coding sequence. The coding sequences of genetic constructs of the invention include functional initiation and termination signals.

As used herein, the term "immunogenic target protein" is meant to refer to an antigen that is a target for an immune response which is directed at proteins associated with conditions, infections, diseases or disorders such as allergens, pathogen antigens, antigens associated with cancer cells or cells involved in autoimmune diseases. The immunogenic target antigen is encoded by the coding sequence of a genetic construct used in a DNA vaccine. The DNA vaccine is administered to the vaccinated individual, the genetic construct is taken up by the cells of the individual, the coding sequence is expressed and the immunogenic target protein is produced. The immunogenic target protein induces an immune response against the immunogenic target protein in the individual. The immune response is directed against proteins associated with conditions, infections, diseases or disorders such as allergens, pathogen antigens, antigens associated with cancer cells or cells involved in autoimmune diseases. Thus the vaccinated individual may be immunized prophylactically or therapeutically to prevent or treat conditions, infections, diseases or disorders. The immunogenic target protein refers to peptides and protein encoded by gene constructs of the present invention which act as target proteins for an immune response. The term "immunogenic target protein" refers to a protein against which an immune response can be elicited. The immunogenic target protein shares at least an epitope with a protein from the allergen, pathogen or undesirable protein or cell-type such as a cancer cell or a cell involved in autoimmune disease against which immunization is required. The immune response directed against the immunogenic target protein will protect the individual against and treat the individual for the specific infection or disease with which the protein from the allergen, pathogen or undesirable protein or cell-type is associated. The immunogenic target protein does not need to be identical to the protein against which an immune response is desired. Rather, the immunogenic target protein must be capable of inducing an immune response that cross reacts to the protein against which the immune response is desired.

As used herein, the term "non-native signal sequence" is meant to refer to signal sequences that are heterologous with respect to the nucleotide sequence that encodes a signal sequence which directs intracellular trafficking of the immunogenic target antigen. A non-native signal sequence is not found linked to the immunogenic target protein in nature but rather is brought about by preparing a gene construct in which the nucleotide sequence that encodes a signal sequence is linked with a nucleotide sequence that encodes the immunogenic target antigen. In some embodiments, a native signal sequence may be removed from a coding sequence that encodes an immunogenic target protein and replaced with a non-native signal sequence to direct the localization of the protein to a location different from the location that the native sequences directs proteins to or to more efficiently direct localization to the same location that the native signal sequence directs localization to.

According to the present invention, the immunogenic target protein includes sequences that direct its localization within the cell. The naturally occurring sequences that direct protein localization may be incorporated into immunogenic target proteins of DNA vaccines by providing signal sequences, designing chimeric proteins or grafting the sequence into the immunogenic protein sequence. The DNA vaccines are plasmids and the coding sequences of the immunogenic target proteins are manipulated by standard molecular biology methodology to produce coding sequences that encode immunogenic target proteins which include signal sequences that direct intracellular protein trafficking, or chimeric immunogenic target proteins that include regions which direct intracellular protein trafficking. Moreover, routine molecular biology techniques may be employed to change the amino acid sequence of an immunogenic target protein so that it contains within its sequence the sequences that direct intracellular protein targeting. In some embodiments, the nucleotide sequence that encodes a signal sequence which directs intracellular trafficking of the immunogenic target antigen is a non-native signal sequence. The nucleotide sequence that encodes a signal sequence of one protein may be identified, isolated and linked to a coding sequence that encodes a different protein using well known techniques.

The location wherein the cell the immunogenic target protein is directed affects the immune response generated by the individual against the immunogenic target protein. It has been discovered that the intracellular targeting of immunogenic target proteins encoded by genetic constructs of DNA vaccines results in an enhanced immune response against the immunogenic target antigen. By providing coding sequence of the intracellular targeting signal as part of the coding sequence of the immunogenic target protein, the immunogenic target protein is localized to a part of the cell. It has been discovered that certain localizations are associated with enhanced specific types of immune responses. For example, it has been discovered that directing protein to be retained or recycled to the endoplasmic reticulum, particularly the rough endoplasmic reticulum results in induction of an enhance CTL response in vaccinated animals relative to that observed using vaccines that do not include sequences that target specific intracellular localization.

The improvement of the present invention relates to the inclusion of genetic material for directing the intracellular localization of immunogenic target proteins produced in cells of individuals administered a DNA vaccine.

The present invention relates to methods of introducing genetic material into the cells of an individual in order to induce immune responses against proteins and peptides which are encoded by the genetic material. The methods comprise the steps of administering to the tissue of said individual, DNA that includes a coding sequence operably linked to regulatory elements required for expression. The coding sequence includes coding sequences for immunogenic target proteins linked to or comprising a coding sequence for an intracellular trafficking signal.

Intracellular trafficking signals are well known.

In some embodiments, proteins are to be secreted. Such proteins include an N-terminal hydrophobic sequence. When RNA is translated, the hydrophobic sequence at the N terminal causes the protein to stick to the rough endoplasmic reticulum. The hydrophobic sequences are subsequently clipped off by a protease and the protein is secreted. In some embodiments of the present invention, the immunogenic target protein may include an N terminal hydrophobic leader sequence which will direct secretion of the immunogenic target protein when expressed in the cell.

In some embodiments, proteins are to be membrane bound. Such proteins include an N-terminal hydrophobic sequence and an internal hydrophobic region. As in the secreted forms, when RNA is translated, the hydrophobic sequences causes the protein to stick to the rough endoplasmic reticulum. The N terminal hydrophobic sequence is subsequently clipped off by a protease. The protein follows the same secretion pathway but the internal hydrophobic sequence prevents secretion and the protein becomes membrane bound. In some embodiments of the present invention, the immunogenic target protein may include an N terminal hydrophobic leader sequence and an internal hydrophobic sequence which will result in the immunogenic target protein becoming a membrane bound protein when expressed in the cell.

In some embodiments, proteins are to be localized in the cytosol. Such proteins do not have an N-terminal hydrophobic sequence. When RNA is translated, the protein does not stick to the rough endoplasmic reticulum and the protein becomes cytosolic. In some embodiments of the present invention, the immunogenic target protein is free of an N terminal hydrophobic leader sequence so that the immunogenic target protein becomes a cytosolic protein when expressed in the cell.

In some embodiments, proteins are to be localized in the lysosome. Such proteins may include the sequence DKQTLL (SEQ ID NO:1) which directs localization of proteins to the lysosome. In some embodiments of the present invention, the immunogenic target protein includes the sequence DKQTLL (SEQ ID NO:1) so that the immunogenic target protein is directed to the lysosome when expressed in the cell.

In some embodiments, proteins are to be localized from the Golgi body back to the ER. Such proteins may include the sequence KDEL (SEQ ID NO:2) at the C terminal which directs localization of proteins to be recycled to the ER. In some embodiments of the present invention, the immunogenic target protein includes the sequence KDEL (SEQ ID NO:2) at the C terminal so that the immunogenic target protein is directed to the ER.

Another example of such an "ER recycling signal" is reported to be the C terminal sequence of the E19 protein from adenovirus. That protein is localized to the ER where it binds to the MHCs and effectively keeps them from loading proteins which are presented by the MHC at the surface where they complex with T cell receptors as part of immune response induction. The E109 protein is a hexapeptide DEKKMP (SEQ ID NO:3). In some embodiments, proteins are to be localized to the ER by including the DEKKMP (SEQ ID NO:3) sequence at the C terminal. In some embodiments of the present invention, the immunogenic target protein includes the sequence DEKKMP (SEQ ID NO:3) at the C terminal so that the immunogenic target protein is directed to the ER.

Depending upon the type of immune response sought to be enhanced, different intracellular localization is desirable. In the case of Class I immune responses, proteins synthesized within a cell are degraded and transported into the ER where they are loaded onto MHCs which then move to the cell surface and complex with T cell receptors of CD8+ T cells. This action leads to CTL responses. In the case of Class II immune responses, proteins are complexed with antigen presenting cells (APCs) which interact with CD4+ T cells, engaging helper T cells including those associated with antibody responses.

In order to enhance Class I immune responses, localization of proteins to the cytosol or ER allows for such proteins to be more accessible to the Class I pathway.

In order to enhance Class II immune responses, localization of proteins to the transmembrane or lysosomes, or secretion of the protein allows such proteins to be more accessible to the Class II pathway.

The present invention provides genetic constructs useful as DNA vaccines that include coding sequences for immunogenic target proteins that comprise sequences for intracellular localization.

In some embodiments, genetic constructs comprise the localization leaders described in Biocca, S. et al. 1990 EMBO J. 9:101–108. The genetic constructs contain those leader sequences in the same orientation as they are described in FIG. 6A. Specifically, the leader sequences occur at the N terminus of the protein directly between the promoter and coding sequence of the protein of interest. In some embodiments, the genetic constructs of the invention comprise one of the leader sequences set forth in FIG. 6A of this application. In some embodiments, the genetic constructs of the invention comprise one of the leader sequences set forth in FIG. 6B of this application.

In some embodiments, genetic constructs comprise the terminal hexapeptide from adenovirus E19 protein for retention in the endoplasmic reticulum. When the C terminus of an immunogenic target protein of a DNA vaccine is DEKKMP (SEQ ID NO:3), the protein will be retained in the ER.

In some embodiments, genetic constructs comprise the C terminal quadrapeptide for retention in the endoplasmic reticulum. When the C terminus of an immunogenic target protein of a DNA vaccine is KDEL (SEQ ID NO:2), the protein will be retained in the ER.

FIGS. 7A and 7B shows several C terminal sequences for ER retention. Jackson, M. R., et al. 1990 EMBO J. 9:3153–3162 reports that C terminal sequences in FIG. 7A, when linked at the C terminal of proteins normally not retained in the ER, results in ER retention of the chimeric protein.

In some embodiments, genetic constructs comprise the lysosomal targeting doublets at the C terminal tail of the immunogenic target protein. The C terminal tail is the last 20–30 amino acids. By including the doublets LL and/or YQ and/or QY the protein is directed to a lysosome. In some embodiments, the C terminal tail which contains one or more lysosome targeting doublets is a cytoplasmic tail of a transmembrane protein. In some embodiments, the doublets are included in the sequence of the immunogenic protein within the last 30 amino acids.

According to the present invention, compositions and methods are provided which prophylactically and/or therapeutically immunize an individual against allergens, pathogens or abnormal, disease-related cells or proteins. The genetic material that encodes a target protein, i.e. a peptide or protein that shares at least an epitope with an immunogenic protein found on the allergen, pathogen or antigen or cell to be targeted, and genetic material that encodes an intracellular trafficking signal. The genetic material is expressed by the individual's cells and serves as an immunogenic target against which an immune response is elicited. The presence of the intracellular trafficking signal directs the localization of the protein to a location in the cell where it is more effective in inducing a desired immune response. The resulting immune response that reacts with the allergen, pathogen or antigens or cells is enhanced relative to the immune response induced by similar genetic constructs which lack the intracellular trafficking signal.

The present invention is useful to elicit immune responses against proteins specifically associated with allergies, pathogens or the individual's own "abnormal" cells. The present invention is useful to immunize individuals against allergens or pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

According to the present invention, DNA encodes an immunogenic target protein that is either linked to an intracellular trafficking signal sequence or a peptide sequence that includes an intracellular trafficking sequence. A signal sequence will be clipped off as part of the cells normal protein processing. In addition, DNA that encodes an immunogenic target protein may include, within the coding sequence of the protein, an intracellular trafficking sequence. Regulatory elements for DNA expression include a promoter and a polyadenylation signal. In addition, other elements, such as a Kozak region, may also be included in the genetic construct.

As used herein, the term "expressible form" refers to gene constructs which contain the necessary regulatory elements operably linked to a coding sequence that encodes an immunogenic target protein such that when present in the cell of the individual, the coding sequence will be expressed.

As used herein, the term "sharing an epitope" refers to proteins which comprise at least one epitope that is identical to or substantially similar to an epitope of another protein.

As used herein, the term "substantially similar epitope" is meant to refer to an epitope that has a structure which is not identical to an epitope of a protein but nonetheless invokes a cellular or humoral immune response which cross reacts to that protein.

Genetic constructs comprise a nucleotide sequence that encodes an immunogenic target protein that includes an intracellular trafficking sequence operably linked to regulatory elements needed for gene expression.

When taken up by a cell, the genetic construct(s) may remain present in the cell as a functioning extrachromosomal molecule and/or integrate into the cell's chromosomal DNA. DNA may be introduced into cells where it remains as separate genetic material in the form of a plasmid or plasmids. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal.

Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the immunogenic target protein. It is necessary that these elements be operably linked to the sequence that encodes the desired proteins and that the regulatory elements are operable in the individual to whom they are administered.

Initiation codons and stop codons are generally considered to be part of a nucleotide sequence that encodes the immunogenic target protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode a target protein, IL-12 protein and, additionally, genes for proteins which further enhance the immune response against such target proteins. Examples of such genes are those which encode cytokines and lymphokines such as α-interferon, gamma-interferon, platelet derived growth factor (PDGF), GC-SF, GM-CSF, TNF, epidermal growth factor (EGF), IL-1, IL-2, IL-4, IL-6, IL-8, IL-10 and B7.2. In some embodiments, it is preferred that the gene for GM-CSF is included in genetic constructs used in immunizing compositions.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs which are functional in the cells.

The method of the present invention comprises the steps of administering nucleic acid molecules to tissue of the individual. In some preferred embodiments, the nucleic acid molecules are administered intramuscularly, intranasally, intraperatoneally, subcutaneously, intradermally, or topically or by lavage to mucosal tissue selected from the group consisting of vaginal, rectal, urethral, buccal and sublingual.

In some embodiments, the nucleic acid molecule is delivered to the cells in conjunction with administration of a facilitating agent. Facilitating agents are also referred to as polynucleotide function enhancers or genetic vaccine facilitator agents. Facilitating agents are described in U.S. Ser. No. 08/008,342 filed Jan. 26, 1993, U.S. Ser. No. 08/029,336 filed Mar. 11, 1993, U.S. Ser. No. 08/125,012 filed Sep. 21, 1993, and International Application Serial Number PCT/US94/00899 filed Jan. 26, 1994, which are each incorporated herein by reference. In addition, facilitating agents are described in PCT application Serial Number PCT/US95/04071 filed Mar. 30, 1995, which is incorporated herein by reference. Facilitating agents which are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with or without a facilitating agent include growth factors, cytokines and lymphokines such as α-interferon, gamma-interferon, platelet derived growth factor (PDGF), GC-SF, GM-CSF, TNF, epidermal growth factor (EGF), IL-1, IL-2, IL-4, IL-6, IL-8, IL-10 and B7.2 as well as fibroblast growth factor, surface active agents such as immune-stimulating complexes (ISCOMS), Freund's incomplete adjuvant, LPS analog including monophosphoryl Lipid A (MPL), muramyl peptides, quinone analogs and vesicles such as squalene and squalene, and hyaluronic acid may also be administered in conjunction with the genetic construct.

In some preferred embodiments, the genetic constructs of the invention are formulated with or administered in conjunction with a facilitator selected from the group consisting of benzoic acid esters, anilides, amidines, urethans and the hydrochloride salts thereof such as those of the family of local anesthetics.

The facilitator in some preferred embodiments may be a compound having one of the following formulae:

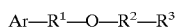

$$Ar-R^1-O-R^2-R^3$$

or

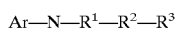

$$Ar-N-R^1-R^2-R^3$$

or

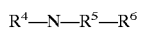

$$R^4-N-R^5-R^6$$

or

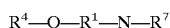

$$R^4-O-R^1-N-R^7$$

wherein:

Ar is benzene, p-aminobenzene, m-aminobenzene, o-aminobenzene, substituted benzene, substituted p-aminobenzene, substituted m-aminobenzene, substituted o-aminobenzene, wherein the amino group in the aminobenzene compounds can be amino, $C_1$–$C_5$ alkylamine, $C_1$–$C_5$, $C_1$–$C_5$ dialkylamine and substitutions in substituted compounds are halogen, $C_1$–$C_5$ alkyl and $C_1$–$C_5$ alkoxy;

$R^1$ is C=O;

$R^2$ is $C_1$–$C_{10}$ alkyl including branched alkyls;

$R^3$ is hydrogen, amine, $C_1$–$C_5$ alkylamine, $C_1$–$C_5$, $C_1$–$C_5$ dialkylamine;

$R^2$+$R^3$ can form a cyclic alkyl, a $C_1$–$C_{10}$ alkyl substituted cyclic alkyl, a cyclic aliphatic amine, a $C_1$–$C_{10}$ alkyl substituted cyclic aliphatic amine, a heterocycle, a $C_1$–$C_{10}$ alkyl substituted heterocycle including a $C_1$–$C_{10}$ alkyl N-substituted heterocycle;

$R^4$ is Ar, $R^2$ or $C_1$–$C_5$ alkoxy, a cyclic alkyl, a $C_1$–$C_{10}$ alkyl substituted cyclic alkyl, a cyclic aliphatic amine, a $C_1$–$C_{10}$ alkyl substituted cyclic aliphatic amine, a heterocycle, a $C_1$–$C_{10}$ alkyl substituted heterocycle and a $C_1$–$C_{10}$ alkoxy substituted heterocycle including a $C_1$–$C_{10}$ alkyl N-substituted heterocycle;

$R^5$ is C=NH;

$R^6$ is Ar, $R^2$ or $C_1$–$C_5$ alkoxy, a cyclic alkyl, a $C_1$–$C_{10}$ alkyl substituted cyclic alkyl, a cyclic aliphatic amine, a $C_1$–$C_{10}$ alkyl substituted cyclic aliphatic amine, a heterocycle, a $C_1$–$C_{10}$ alkyl substituted heterocycle and a $C_1$–$C_{10}$ alkoxy substituted heterocycle including a $C_1$–$C_{10}$ alkyl N-substituted heterocycle; and.

$R^7$ is Ar, $R^2$ or $C_1$–$C_5$ alkoxy, a cyclic alkyl, a $C_1$–$C_{10}$ alkyl substituted cyclic alkyl, a cyclic aliphatic amine, a $C_1$–$C_{10}$ alkyl substituted cyclic aliphatic amine, a heterocycle, a $C_1$–$C_{10}$ alkyl substituted heterocycle and a $C_1$–$C_{10}$ alkoxy substituted heterocycle including a $C_1$–$C_{10}$ alkyl N-substituted heterocycle.

Examples of esters include: benzoic acid esters such as piperocaine, meprylcaine and isobucaine; para-aminobenzoic acid esters such as procaine, tetracaine, butethamine, propoxycaine and chloroprocaine; meta-aminobenzoic acid esters including metabuthamine and primacaine; and para-ethoxybenzoic acid esters such as parethoxycaine. Examples of anilides include lidocaine, etidocaine, mepivacaine, bupivacaine, pyrrocaine and prilocaine. Other examples of such compounds include dibucaine, benzocaine, dyclonine, pramoxine, proparacaine, butacaine, benoxinate, carbocaine, methyl bupivacaine, butasin picrate, phenacaine, diothan, luccaine, intracaine, nupercaine, metabutoxycaine, piridocaine, biphenamine and the botanically-derived bicyclics such as cocaine, cinnamoylcocaine, truxilline and cocaethylene and all such compounds complexed with hydrochloride.

In preferred embodiments, the facilitator is bupivacaine. The difference between bupivacaine and mepivacaine is that bupivacaine has a N-butyl group in place of an N-methyl group of mepivacaine. Compounds may have at that N, $C_1$–$C_{10}$. Compounds may be substituted by halogen such as procaine and chloroprocaine. The anilides are preferred.

The facilitating agent is administered prior to, simultaneously with or subsequent to the genetic construct. The facilitating agent and the genetic construct may be formulated in the same composition.

Bupivacaine-HCl is chemically designated as 2-piperidinecarboxamide, 1-butyl-N-(2,6-dimethylphenyl)-monohydrochloride, monohydrate and is widely available commercially for pharmaceutical uses from many sources including from Astra Pharmaceutical Products Inc. (Westboro, Mass.) and Sanofi Winthrop Pharmaceuticals (New York, N.Y.), Eastman Kodak (Rochester, N.Y.). Bupivacaine is commercially formulated with and without methylparaben and with or without epinephrine. Any such formulation may be used. It is commercially available for pharmaceutical use in concentration of 0.25%, 0.5% and 0.75% which may be used on the invention. Alternative concentrations, particularly those between 0.05%–1.0% which elicit desirable effects may be prepared if desired. According to the present invention, about 250 μg to about 10 mg of bupivacaine is administered. In some embodiments, about 250 μg to about 7.5 mg is administered. In some embodiments, about 0.05 mg to about 5.0 mg is administered. In some embodiments, about 0.5 mg to about 3.0 mg is administered. In some embodiments about 5 to 50 μg is administered. For example, in some embodiments about 50 μl to about 2 ml, preferably 50 μl to about 1500 μl and more preferably about 1 ml of 0.25–0.50% bupivacaine-HCl and 0.1% methylparaben in an isotonic pharmaceutical carrier is administered at the same site as the vaccine before, simultaneously with or after the vaccine is administered. Similarly, in some embodiments, about 50 μl to about 2 ml, preferably 50 μl to about 1500 μl and more preferably about 1 ml of 0.25–0.50% bupivacaine-HCl in an isotonic pharmaceutical carrier is administered at the same site as the vaccine before, simultaneously with or after the vaccine is administered. Bupivacaine and any other similarly acting compounds, particularly those of the related family of local anesthetics may be administered at concentrations which provide the desired facilitation of uptake of genetic constructs by cells.

In some embodiments of the invention, the individual is first subject to injection of the facilitator prior to administration of the genetic construct. That is, for example, up to a about a week to ten days prior to administration of the genetic construct, the individual is first injected with the facilitator. In some embodiments, the individual is injected with the facilitator about 1 to 5 days; in some embodiments 24 hours, before or after administration of the genetic construct. Alternatively, if used at all, the facilitator is administered simultaneously, minutes before or after administration of the genetic construct. Accordingly, the facilitator and the genetic construct may be combined to form a single pharmaceutical composition.

In some embodiments, the genetic constructs are administered free of facilitating agents, that is in formulations free from facilitating agents using administration protocols in which the genetic constructions are not administered in conjunction with the administration of facilitating agents.

Nucleic acid molecules which are delivered to cells according to the invention may serve as genetic templates for proteins that function as prophylactic and/or therapeutic immunizing agents. In preferred embodiments, the nucleic acid molecules comprise the necessary regulatory sequences for transcription and translation of the coding region in the cells of the animal.

The present invention may be used to immunize an individual against all pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhea, listeria and shigella. In addition, the present invention is also useful to immunize an individual against protozoan pathogens which include a stage in the life cycle where they are intracellular pathogens. As used herein, the term "intracellular pathogen" is meant to refer to a virus or pathogenic organism that, at least part of its reproductive or life cycle, exists within a host cell and therein produces or causes to be produced, pathogen proteins. Table 1 provides a listing of some of the viral families and genera for which vaccines according to the present invention can be made. DNA constructs that comprise DNA sequences which encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 2.

In order to produce a genetic vaccine to protect against pathogen infection, genetic material which encodes immunogenic proteins against which a protective immune response can be mounted must be included in a genetic construct as the coding sequence for the target. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The genetic construct used in the genetic vaccine can include genetic material which encodes many pathogen antigens. For example, several viral genes may be included in a single construct thereby providing multiple targets.

Tables 1 and 2 include lists of some of the pathogenic agents and organisms for which genetic vaccines can be prepared to protect an individual from infection by them. In some preferred embodiments, the methods of immunizing an individual against a pathogen are directed against HIV, HTLV or HBV.

Another aspect of the present invention provides a method of conferring a broad based protective immune response against hyperproliferating cells that are characteristic in hyperproliferative diseases and to a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer and psoriasis.

It has been discovered that introduction of a genetic construct that includes a nucleotide sequence which encodes an immunogenic "hyperproliferating cell"-associated protein into the cells of an individual results in the production of those proteins in the vaccinated cells of an individual. As used herein, the term "hyperproliferative-associated protein" is meant to refer to proteins that are associated with a hyperproliferative disease. To immunize against hyperproliferative diseases, a genetic construct that includes a nucleotide sequence which encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P5S3, neu, trk and EGRF. In addition to oncogene products as target antigens, target proteins for anti-cancer treatments and protective regimens include variable regions of antibodies made by B cell lymphomas and variable regions of T cell receptors of T cell lymphomas which, in some embodiments, are also used to target antigens for autoimmune disease. Other tumor-associated proteins can be used as target proteins such as proteins which are found at higher levels in tumor cells including the protein recognized by monoclonal antibody 17-1A and folate binding proteins.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in the individual. Using genetic screening and/or family health histories, it is possible to predict the probability a particular individual for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include Vβ-3, Vβ-14, Vβ-17 and Vα-17. Thus, vaccination with a DNA construct that encodes at least one of these proteins will elicit an immune response that will target T cells involved in RA. See: Howell, M. D., et al., 1991 *Proc. Natl. Acad. Sci. U.S.A.* 88:10921–10925; Paliard, X., et al., 1991 *Science* 253:325–329; Williams, W. V., et al., 1992 *J. Clin. Invest.* 90:326–333; each of which is incorporated herein by reference.

In MS, several specific variable regions of TCRs which are involved in the disease have been characterized. These TCRs include Vβ-7 and Vα-10. Thus, vaccination with a DNA construct that encodes at least one of these proteins will elicit an immune response that will target T cells involved in MS. See: Wucherpfennig, K. W., et al., 1990 *Science* 248:1016–1019; Oksenberg, J. R., et al., 1990 *Nature* 345:344–346; each of which is incorporated herein by reference.

In scleroderma, several specific variable regions of TCRs which are involved in the disease have been characterized. These TCRs include Vβ-6, Vβ-8, Vβ-14 and Vα-16, Vα-3C, Vα-7, Vα-14, Vα-15, Vα-16, Vα-28 and Vα-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al. 1987 *Sequence of Proteins of Immunological Interest U.S. Department of Health and Human Services,* Bethesda Md., which is incorporated herein by reference. In addition, a general method for cloning functional variable regions from antibodies can be found in Chaudhary, V. K., et al., 1990 *Proc. Natl. Acad. Sci. U.S.A.* 87:1066, which is incorporated herein by reference.

EXAMPLES

Example 1

Nephritogenic Autoantibody anti-DNA IL/IM

This mAb was identified from a large panel of hybridomas derived from MRL-lpr/lpr mice (Vlahakos, et al., 1992 Kidney Int 41,1690–1700) because it shared antigen binding properties with Ig eluted from the kidneys of MRL-lpr/lpr mice with nephritis. Anti-DNA IL/IM is an IgG2a antibody of the J558 VH gene family with a pI of 5.1. Anti-DNA IL/IM Ab specifically binds to ssDNA, dsDNA, SmRNP, and glomerular extract. Following administration to normal, histocompatible mice, anti-DNA IL/IM forms mesangial, subendothelial and intraluminal immune deposits in the kidneys. When anti-DNA IL/IM producing hybridoma cells are administered intraperitoneally to histocompatible mice, they produce dense intramembranous and intraluminal deposits, associated with capillary wall thickening, mesangial interposition and expansion, aneurysmal dilatation and intraluminal occlusion of glomerular capillary loops, and heavy proteinuria. Although the morphologic appearance of the glomerular immune deposits are reminiscent of those associated with cryoglobulinemia, anti-DNA IL/IM hybridoma-bearing mice with high serum anti-DNA Ab activity did not have detectable cryoglobulins or rheumatoid factor activity. Glomerular immune deposit formation was associated with capillary wall thickening, mesangial interposition and expansion, aneurysmal dilitation and intraluminal occlusion of glomerular capillary loops, and heavy proteinuria.

Given its cross-reactive and distinctive nephritogenic properties, an analysis of whether anti-DNA-IL/IM formed immune deposits by direct interaction with glomerular Ag was considered. To address this possibility, the capacity of monoclonal anti-DNA IgG2a Ab, anti-DNA IL/IM to bind to glomerular cell surface antigens was evaluated. Anti-DNA IL/IM produced mesangial, subendothelial and intraluminal deposits, in vivo after administration to normal mice. By FACS, anti-DNA IL/IM (referred to by hybridoma number H221) bound to mesangial, tubular epithelial and aortic endothelial cell surfaces, whereas surface binding by isotype-matched anti-DNA antibodies that did not produce glomerular immune deposits, was not observed. The results are illustrated in FIG. 1. (Murine endothelial cells were the kind gift of Dr. Fuad Ziyadeh, Renal Division, University of Pennsylvania.)

Western blots using total cell lysates of component lomerular cells probed with anti-DNA antibodies showed hat anti-DNA IL/IM reacted with multiple bands, whereas anti-DNA antibodies that did not form immune deposits did not. Following biotinylation of cell surface antigen and immunoprecipitation with anti-DNA IL/IM, a 100 kD band within mesangial cell lysates was identified that was not recognized by an isotype matched control monoclonal anti-DNA antibody.

Thus, anti-DNA IL/IM mAb was demonstrated to bind to murine renal mesangial cells and aortic endothelial cells, and a candidate surface protein target has been identified. This indicates the polyspecific antigen binding properties of this mAb, which is a common feature of pathogenic SLE antibodies, and may be responsible for binding to cell surface antigens in the initiation of glomerular immune deposit formation.

Sequence analysis of anti-DNA IL/IM (H221) has been carried out. The complete VL-JL sequence (SEQ ID NO:4) and a near complete sequence of the VH-DH-JH (SEQ ID NO:6) are shown here.

The results confirm that anti-DNA IL/IM (H221) is a member of the J558 VH family and provides reagents to perform the experiments described in the Research Design and Methods section. Additional sequence analysis is underway to complete the sequence of the heavy chain.

Genetic Immunization Against Anti-DNA IL/IM

Figures 2A, 2B:
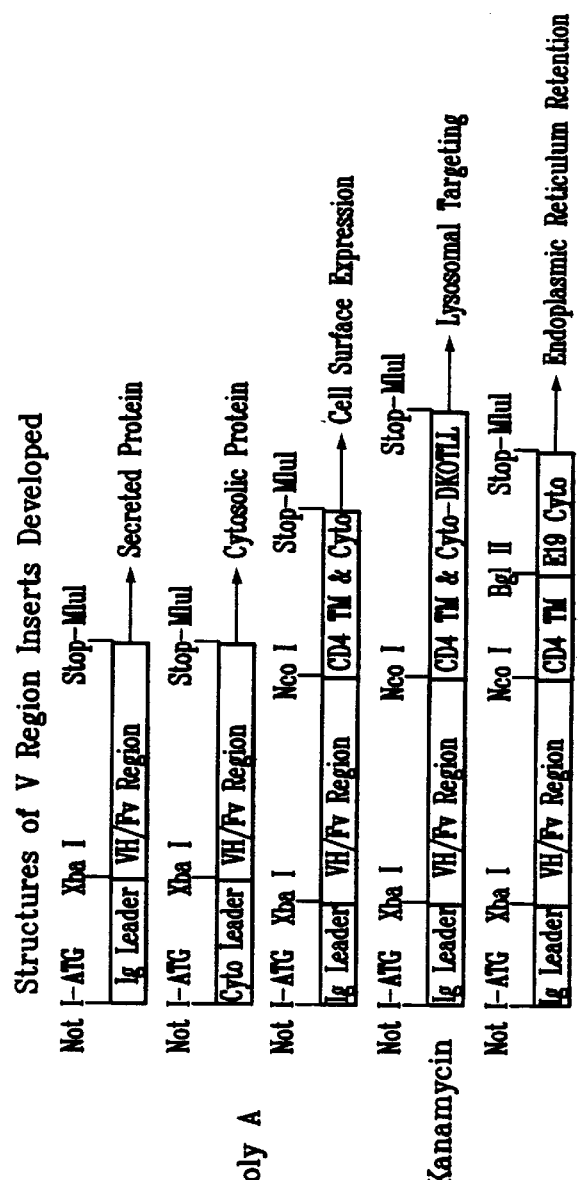
FIG. 2A shows a map of the genetic immunization vector into which the VH or Fv regions were cloned.
FIG. 2B shows a map of the constructions of inserts that encode the V regions used to target the V regions to different locations in the cell.

Preliminary studies have been performed immunizing AKR×DBA/2 mice with DNA constructs encoding the anti-DNA IL/IM VH or Fv regions and then challenging them with a lethal dose of the parent hybridoma cells. Briefly, as shown in FIG. 2A, the VH or Fv regions were cloned into the genetic immunization vector placing the V regions under control of the CMV promoter. As described in FIG. 2B, the V regions were targeted either to the cell membrane, to be secreted, to remain in the cytosol, or to be retained in the endoplasmic reticulum using the adenovirus E19 protein ER retention signal. Constructs targeted to the lysosomes were also developed.

Biocca, S. et al. 1990 EMBO J. 9(l):101–108, which is incorporated herein by reference describes targeting to the cell membrane, secretion, cytosolic localization. Nilsson et al. 1989 Cell 58:707–718, Jackson et al. 1993 J. Cell Biol. 121(2)317–333, and Jackson et al 1990 EMBO J. 9:3153–3162 described proteins retained in the endoplasmic reticulum using the adenovirus E19 protein ER retention

H221 VL-JL Sequence (SEQ ID NO:4)

```
GAC ATT GTG ATA TCA CAG TCT CCA TCC ACC CTG GCT GTG TCA GCA GGA GAG AAG GTC ACT ATG AAC
asp ile val ile ser gln ser pro ser thr leu ala val ser ala gly glu lys val thr met asn
                                    CDR I
TGC AAA TCC AGT CAG AGT CTG TTC AAC AGT AGA ACC CGA AAG AAC TAC TTG GCT TGG TTC CAG CAG
cys lys ser ser gln ser leu phe asn ser arg thr arg lys asn tyr leu ala trp phe gln gln
                                                              CDR II
AAA CCA GGG CAG TCT CCT AAA CTG CTG ATC TAC TGG GCA TCC ACT AGG GAA TCT GGG GTC CCT GAT
lys pro gly gln ser pro lys leu leu ile tyr trp ala ser thr arg glu ser gly val pro asp CGC TTC ACA GGC AGT GGA TCT GGG ACA GAT TTC ACT CTC ACC ATC AGC AGT GTG CAG GCT GAA GAC
arg phe thr gly ser gly ser gly thr asp phe thr leu thr ile ser ser val gln ala glu asp
                                    CDR III
CTG GCA GTT TAT TAC TGC AAG CAA TCT TAT TAT CTT CGG ACG TTC GGT GGA GGC ACC AGG CTG GAA
leu ala val tyr tyr cys lys gln ser tyr tyr leu arg thr phe gly gly gly thr arg leu glu
```

H221 VH-DH-JH Sequence (SEQ ID NO:6)

```
GAG GTC CAG CTG CAG CAG CCT GGT GCT GAA CTT GTG AAG TCT GGG GCC TCA GTG AAG CTG
glu val gln leu gln gln pro gly ala glu leu val lys ser gly ala ser val lys leu
                                    CDR I
TCC TGC AAG GCT TCT GAC TTC ACT TTC ACC AGC TAC TGG ATA AAC TGG GTG AAA CAG AGG
ser cys lys ala ser asp phe thr phe thr ser tyr trp ile asn trp val lys gln arg
                                                              CDR II
CCT GGA CAA GGC CTT GAG TGG ATT GGA AAA TTT TAT CCT GGT AGT GGT ACT ATT AAC TAC
pro gly gln gly leu glu trp ile gly lys phe tyr pro gly ser gly thr ile asn tyr AGT GAA AAT TTT AAG AAA AAG GCC ACA CTG ACT GTA GAC ACA TCC TCC AGT ACA TCC TAC
ser glu asn phe lys lys lys ala thr leu thr val asp thr ser ser ser thr ser tyr ATG CAG CTC AGC AGC CTG ACA TCT GAC GAC TCT GCG GTC TAT TAT TGT GCA AGA GAA CGT
met gln leu ser ser leu thr ser asp asp ser ala val tyr tyr cys ala arg glu arg
   CDR III
CTC CTG GGG TTT GTT TAT TGG GGC CAA GGG ACT CTG GTC ACT GTC TCT ACA GCC AAA ACA
leu leu gly phe val tyr trp gly gln gly thr leu val thr val ser thr ala lys thr ACA GCC CCA TCG GTC TAT CGG GGA TCC TCT AGA GTC GAC CTG CAG GCA TGC AAG CTT GGC ACT
thr ala pro ser val tyr arg gly ser ser arg val asp leu gln ala cys lys leu gly thr
``` signal. Letourneur, F. and R. D. Klausner 1992 Cell 69:1143–1157 describe proteins targeted to the lysosomes.

In preliminary experiments, purified plasmid DNA was inoculated into mice following Bupivacaine pretreatment, and following several boosts the mice were evaluated for antibody responses. Controls included killed hybridoma cells and purified antibody Fv regions. None of these immunogens was capable of eliciting a serologic response against anti-DNA IL/IM Fab fragments (detection was with labeled Staph. protein G). In preliminary studies, proliferative and cytotoxic T cell responses were elicited with several of the constructs. The best constructs were selected for evaluation in a larger group of mice. Groups of four AKR×DBA/2 mice were immunized once with 100 μg plasmid DNA with Bupivacaine simultaneously. One week later, they were sacrificed and evaluated for cytotoxic T cell and proliferative responses.

Figure 3:
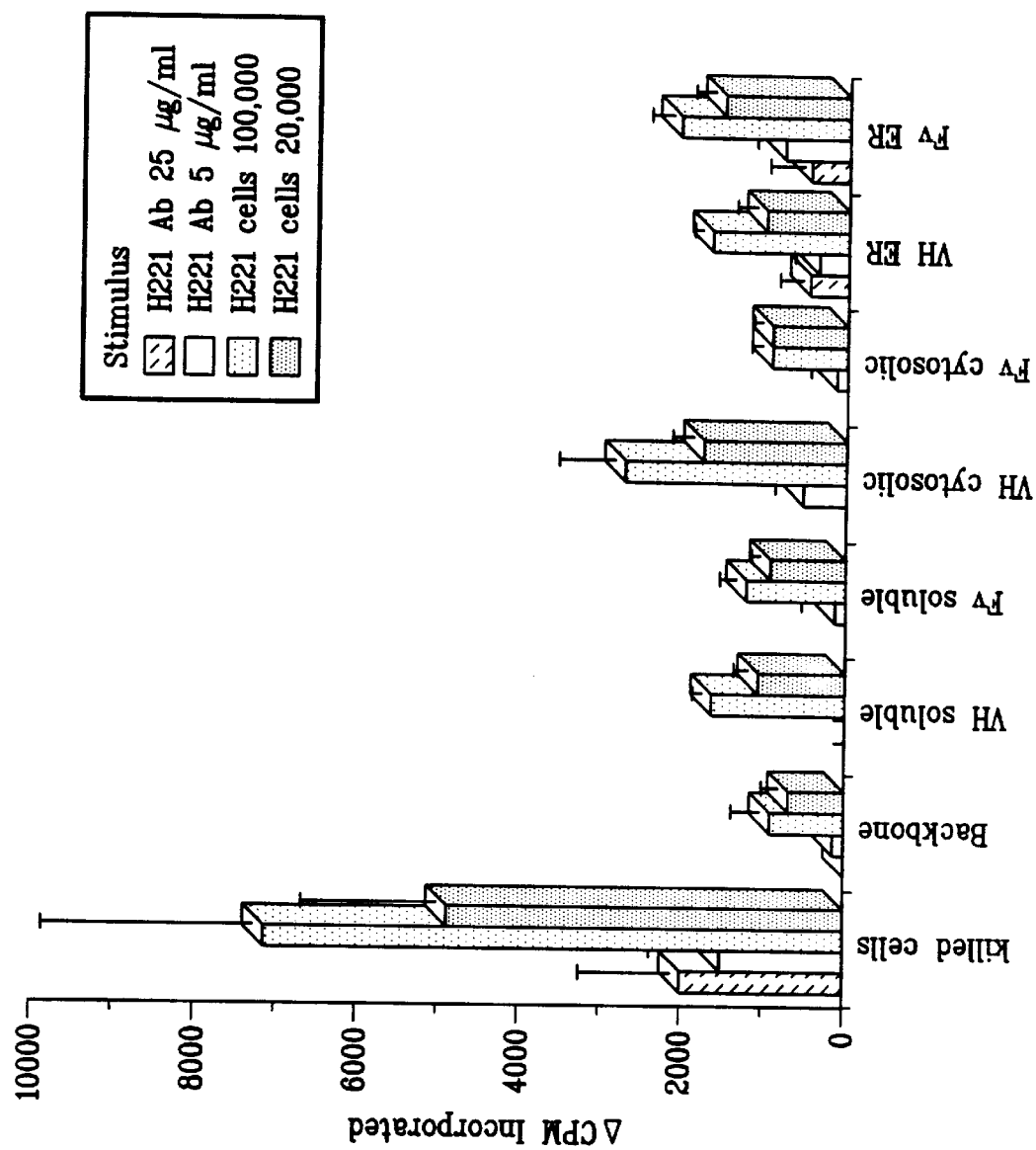
FIG. 3 shows results of experiments in which the different construct designed to be targeted at various locations within the cell were compared for their induction of cytotoxic T cell and proliferative responses.

Proliferation was evaluated by stimulating the immune spleenocytes with either purified H221 mAb (25 or 5=B5g/well) or with 20,000 or 100,000 killed anti-DNA IL/IM hybridoma cells for 72 hours, followed by a pulse with tritiated thymidine overnight. The results are shown in FIG. 3.

Figure 4A:
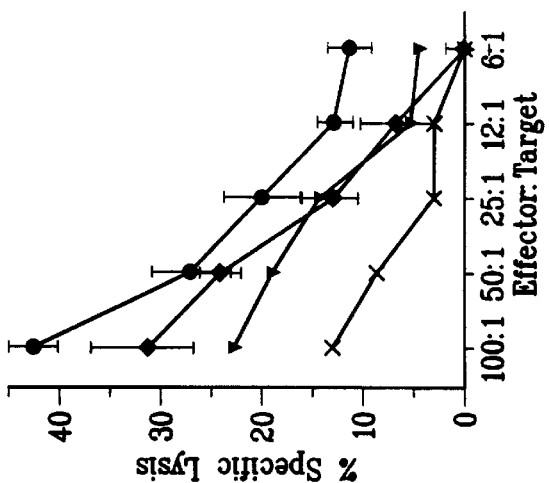
FIGS. 4A, 4B and 4C show results from experiments evaluating CTL responses elicited by various intracellular targeted DNA vaccines.
Figure 4B:
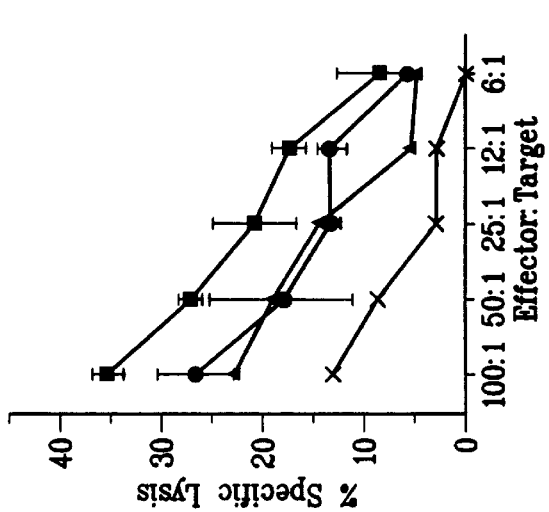
Figure 4C:
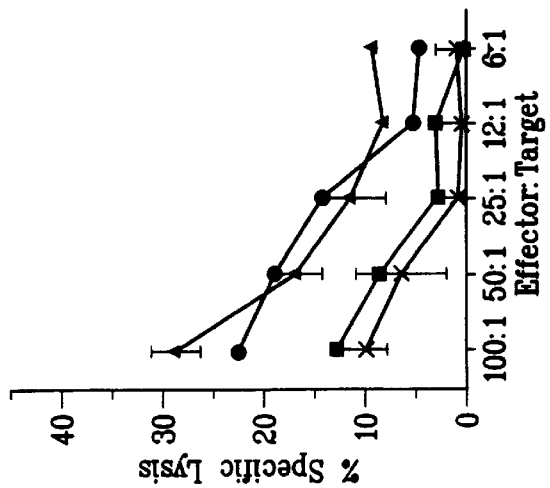

The best proliferative response was induced by the killed hybridoma cells. Measurable responses (compared with vector only) were seen for most constructs, but were only modest in magnitude. The proliferative responses against purified mAb were significant (>2 standard errors above the backbone control) for the mice immunized with killed cells or with the ER-targeted vaccines. The proliferative responses against the hybridoma cells were significant (>2 standard errors above the backbone control) for both ER-targeted vaccines, and the VH-soluble and VH-cytosolic vaccines. In contrast, the CTL responses elicited were striking. These results are shown in FIGS. 4A, 4B and 4C.

The immune spleen cells were cultured for 7 days in the presence of killed anti-DNA IL/IM stimulators (20:1 ratio of spleen cells to stimulators), in the presence of concanavalin A for the first 2 days, then with stimulators only. The anti-DNA IL/IM hybridoma cells were labeled with 51Cr, and lysis determined in round bottomed microtiter plates. The mean =B1 standard deviation % specific lysis (as noted above for CD4) is shown for various effector: target ratios. Interestingly, all of the constructs except one (soluble heavy chain V region or VH sol) elicited CTL activity as good or better than killed cells, which was the positive control for the assay. In particular, exceptional responses were seen for the cytosolic and ER targeted constructs. This indicates that targeting to these compartments boosts the CTL responses seen.

These studies indicate good to excellent induction of CTL responses by most of the DNA vaccines evaluated. This experiment can serve as an example of the strategy used to select particular vaccines to carry on in the study while excluding other. Thus, the Fv construct targeted to the cytosol elicited a CTL response that was clearly higher (>2 standard errors) than the other constructs. Based on this analysis, this vaccine invites further evaluation. Similarly, the VH soluble vaccine did not elicit a good CTL response. Therefore, this vaccine would be eliminated from further analysis, as it would not be expected to elicit protective responses based on the hypotheses generated in the CD4 system.

An additional experiment with this vaccine revealed that this was indeed the case. In this experiment, groups of 5 or 6 mice were immunized 3 times with 100=B5g's of the DNA vaccines. They were then challenged with anti-DNA IL/IM hybridoma cells intraperitoneally. Four weeks later, when tumors developed in the control animals, all of the mice were sacrificed and evaluated for tumor burden and amount of ascites. The proportion of mice developing tumors was also quantified. The results are shown in FIGS. 5A, 5B and 5C.

Figure 5A:
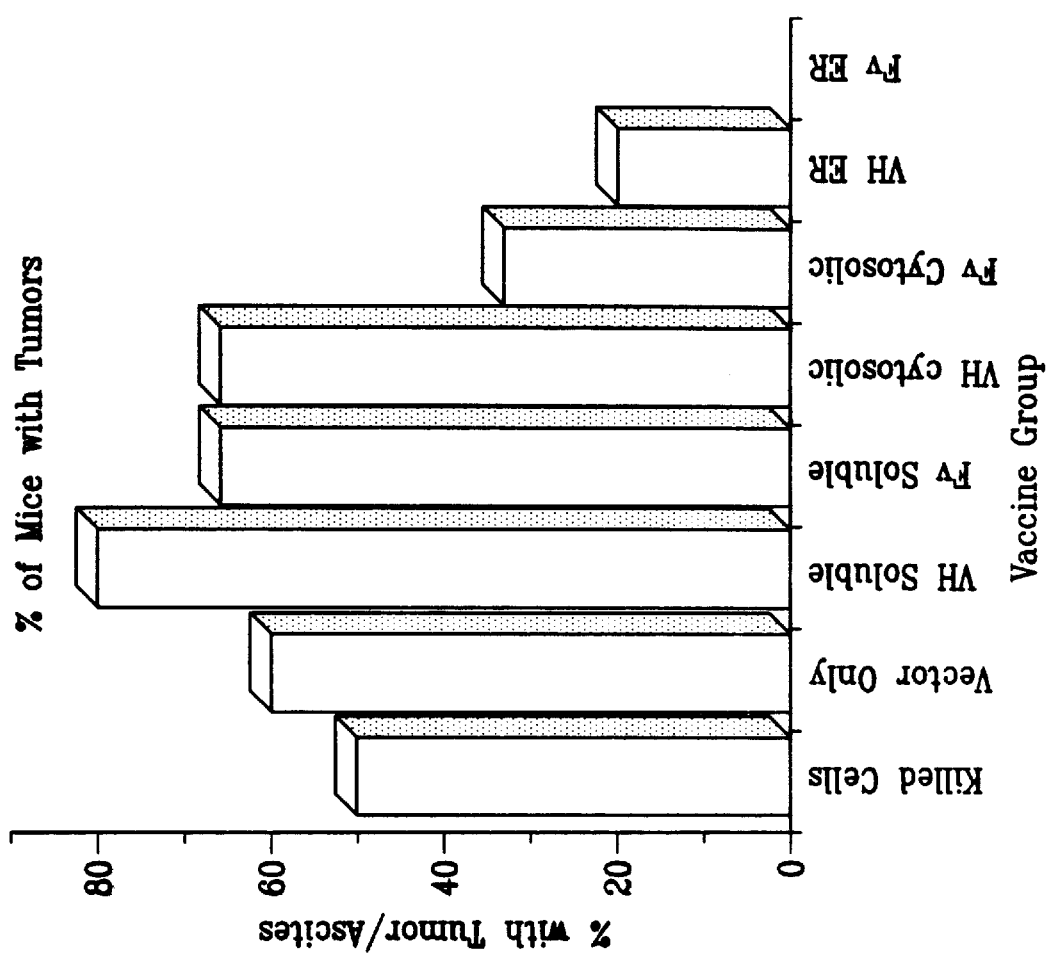
FIGS 5A, 5B and 5C show results from tumor challenge experiments using hybridoma cells that produce the antibody whose variable region is encoded by the DNA vaccine.
Figure 5B:
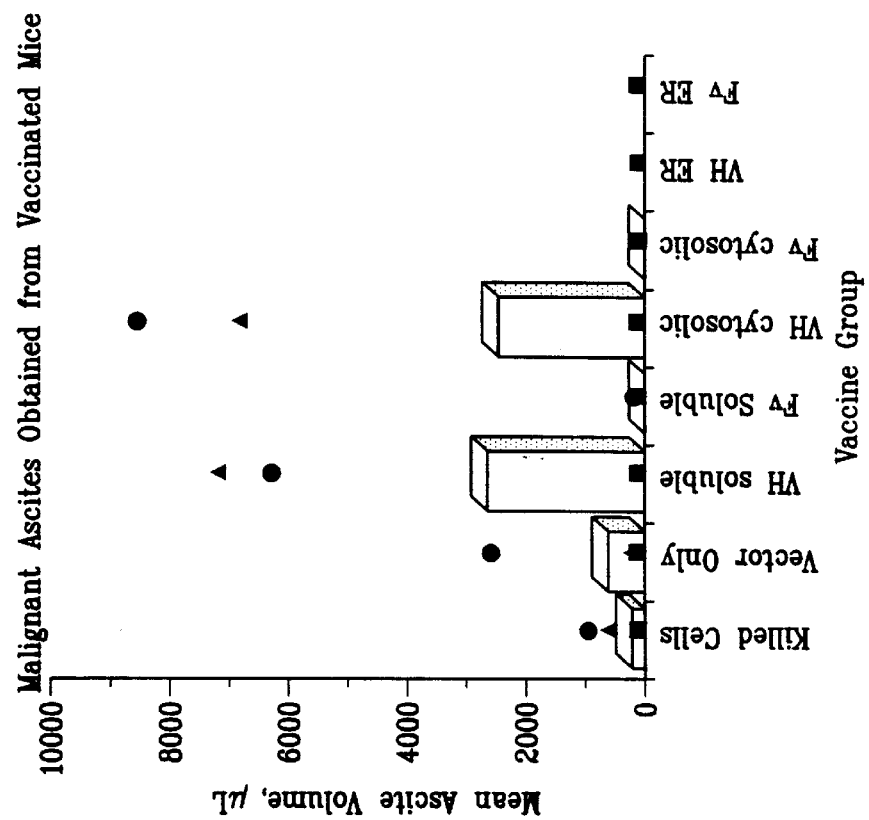
Figure 5C:
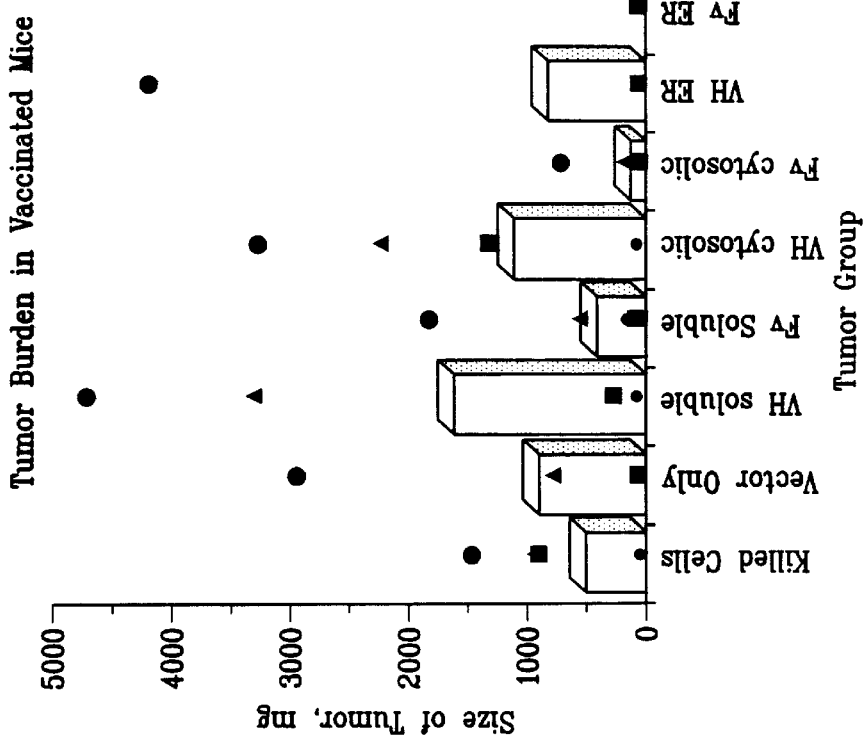

FIG. 5A shows the proportion of mice in which tumors developed. FIG. 5B shows the mean tumor mass in the groups, as well as the values for individual mice. FIG. 5C similarly shows the volume of malignant ascites obtained. Note that in this particular experiment, mice immunized with killed cells (our positive control) did not differ very much from mice immunized with vector only (our negative control) by any measure. In spite of this, several of the DNA vaccines showed clear protective ability, particularly the FV cytosolic targeted vaccine and both the FV and VH endoplasmic reticulum (ER) targeted vaccines. This correlates fairly well with these vaccines, ability to elicit CTL responses. The VH soluble vaccine showed no protective activity, which correlates with its failure to show CTL activity.

Example 2

Several human diseases are associated with pathologic proliferation of B and T cells. This includes malignancies or hyperproliferative diseases such as lymphoma and leukemia, and autoimmune diseases, such as Systemic Lupus Erythematosus (SLE) where pathogenic autoantibodies mediate tissue injury. Current therapy for these diseases is inadequate and treatment is associated with a high incidence of side-effects. A more logical approach to therapy for such diseases is to specifically eliminate the pathogenic cells. This might be accomplished by active immunotherapy targeting their variable regions. Active immunization against V regions has the potential of eliminating the pathogenic cells. Furthermore, by eliciting protective immunity, reemergence of pathogenic clones can be eliminated. However, the immune response elicited by immunization also has the potential to produce detrimental consequences. For example, ideally vaccination against autoantibody producing B cell V regions should elicit cytotoxic T cell (CTL) responses, deleting the pathogenic B cells, limiting autoantibody production. If however helper T cells, (i.e. $TH_2$ type responses) were elicited, autoantibody production might in fact be increased to the detriment of the patient. Therefore, active immunization against pathogenic B or T cell V regions should be designed to elicit desired immune responses (such as CTL responses), while limiting potentially detrimental responses (such as $TH_2$ responses).

DNA vaccination against an autoantibody V region has been evaluated as follows. The autoantibody-producing hybridoma anti-DNA IL/IM (also called H221) was selected from a large panel of hybridomas derived from MRL-lpr/lpr mice; when anti-DNA IL/IM producing hybridoma cells are administered intraperitoneally to histocompatible mice, they produce glomerulonephritis, characterized by dense intramembranous and intraluminal deposits, associated with capillary wall thickening, mesangial interposition and expansion, aneurysmal dilation and intraluminal occlusion of glomerular capillary loops, and heavy proteinuria. This provided an in vivo system in which the efficacy of idiotypic DNA vaccination targeting a pathogenic autoantibody V region in eliciting protective immunity was evaluated. To investigate the possibility of enhancing the immunogenicity of these DNA vaccines, gene expression was targeted to specific intracellular versus extracellular compartments (cytosolic, endoplasmic reticulum (ER) for secretion and ER for retention). Vaccination against a single V region (the $V_H$ region) and against the entire Fv ($V_H$ linked to $V_L$) fragment were employed. The results indicate that DNA inoculation against the H221 $V_H$ and Fv regions elicits specific cellular immune responses, particularly potent CTL responses, with enhancement in CTL activity by targeting the V region to be expressed in the cytosol or to be retained in the ER. Furthermore, idiotypic DNA vaccination elicited protective immunity against H221 cells, particularly when the gene product was targeted for retention in the ER.

Materials and Methods

Figure 8:
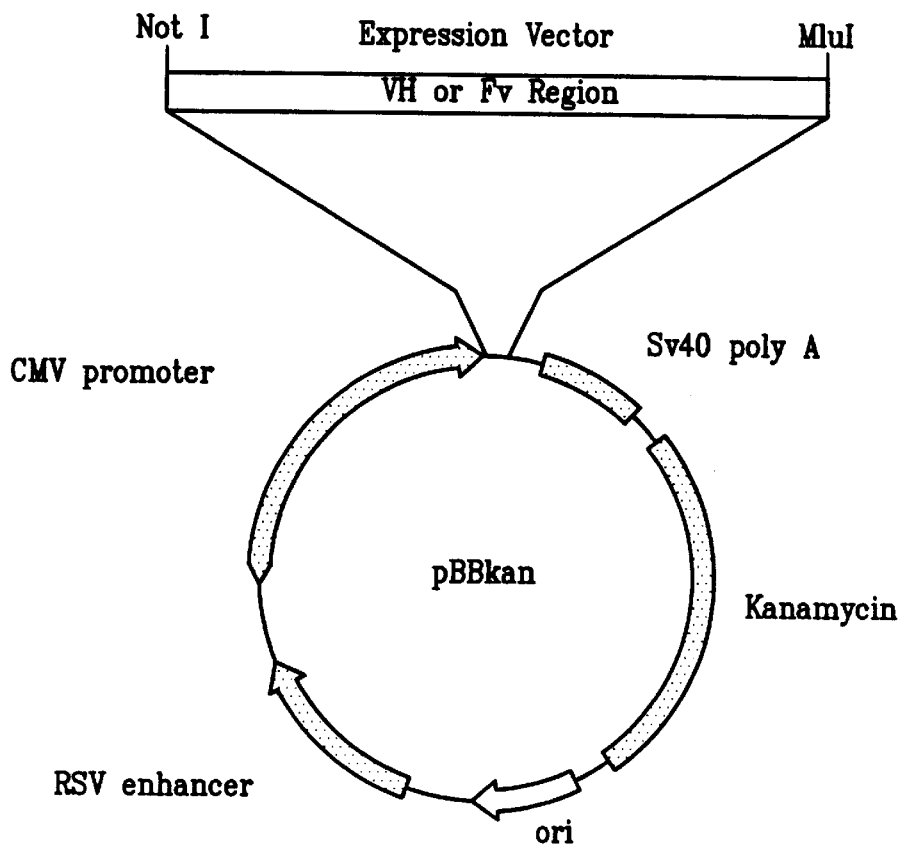
FIG. 8 shows the structure of DNA Vaccines. The DNA Vaccine backbone used was the pBBkan backbone. This uses the CMV promoter and RSV enhancer to drive transcription. The inserts are shown in Table 4, with $V_H$ Fv ($V_L$ linked to $V_H$) regions following a leader peptide (either a hydrophobic leader from murine IgG (Ig Leader), or a hydrophilic leader for cytosolic targeting (Cyto Leader)), and an added transmembrane and cytosolic tail with an endoplasmic reticulum retention signal (CD4 TM & E19 Cyto).
Figure 8:
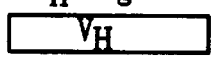
Figure 8:

DNA Constructs pBBkan is a eukaryotic expression vector which utilizes a CMV promoter and an RSV enhancer to direct transcription (FIG. 8). This was initially modified by subcloning a secretory leader from mouse IgG or a cytoplasmic leader into the multiple cloning site between the NotI and XbaI sites. The vector with the secretory leader was the parent vector for the secreted and the ER-retained vaccines. Likewise, the vector with the cytoplasmic leader was the parent vector for the cytoplasmically expressed vaccines. The H221 $V_H$ and $V_L$ regions were amplified by the polymerase chain reaction (PCR) and recombinant PCR was used to generate the Fv coding sequences (Srikatan, et al. 1994 AIDS 8:1525–32, which is incorporated herein by reference). An XbaI restriction site was cloned into the 5' end of the single heavy chain products and the 5' end of the kappa light chain product (Fv). The CPR products were restriction digested and then purified from 2% low-melting agarose by standard phenol-chloroform extraction, gel purified and either ligated directly into the vector (as with the leader sequences) or ligated to other fragments and used as templates for further PCR reactions splicing on the 3' targeting sequences (CD4 TM to E19, Fv or Vh to CD4-E19) where indicated. The E19 signal sequence was amplified from a CD8-E19 (Nilsson, et al. 1989 CELL 58:707–718, which is incorporated herein by reference). The primers used are listed in Table 3. The amino acid sequences for the Immunoglobulin Leader (ER Targeting for Secretion or Retention) (SEQ ID NO:22), Cytosolic Leader (SEQ ID NO:23), H221 VL Region (SEQ ID NO:24), Linker Peptide (SEQ ID NO:25), H221 VH Region (SEQ ID NO:26) and CD4 transmembrane and E19 Cytoplasmic Domains (for ER Retention) (SEQ ID NO:27) are listed in Table 4. The Immunoglobulin Leader (SEQ ID NO:22) was a murine immunoglobulin leader that was used to target the gene product to the ER for secretion or ER retention. The Cytosolic Leader (SEQ ID NO:23) was a sequence previously reported for intracellular expression of antibodies (Biocca, et al. 1990 EMBO J. 9:101–108, which is incorporated herein by reference). The VH and VL sequences (SEQ ID NO:24 and SEQ ID NO:26, respectively) were determined following cloning of the PCR products. The Linker Peptide (SEQ ID NO:25) was used for functional expression of Fv regions. The human CD4 transmembrane region was combined with the adenovirus E19 Targeting sequence for ER retention (SEQ ID NO:27).

These PCR products were cloned into pBBkan and transformed into DH5 alpha *E. coli* (Life Technologies Inc., Gaithersburg, Md.) and clones with correct restriction patterns were sequenced with the ABI fluorescent sequencing kit (Applied Biosystems Inc., Foster City, Calif.). Products were purified and dried as per kit instructions and gel running and analysis were performed by the University of Pennsylvania Cancer Center Core sequencing Facility. Sequence analysis reveals that H221 utilizes the J558 $V_H$ and $J_H3$ genes, paired with the VK1 genes. The vector, constructs, and insert sequences are shown in FIG. 8 and Table 4. Plasmid preparations were grown in Super Broth (1.2% w/v Difco tryptone, 2.4% w/v Difco yeast extract, 0.5% v/v glycerol, 72 mM potassium phosphate dibasic, 28 mM potassium phosphate monobasic) and purified using Qiagen 500 tips according to the manufacturer's protocol (Qiagen Inc., Chatsworth, Calif.). DNA inoculation was carried out with bupivacaine pre-treatment (Wang, et al. 1993 Proc. Natl. Acad. Sci. U.S.A. 90:4156–4160, which is incorporated herein by reference).

Proliferation Assay

Individual spleens from the vaccinated mice are extracted in a sterile fashion, gently disrupted in RPMI and treated with Gey's solution to lyse the red blood cells. Splenocytes are plated in 96-well flat-bottom tissue culture plates (Falcon 3072; Becton Dickinson, Franklin Lakes, N.J.) at 500,000 per well in a 200 $\mu$L final volume. Triplicate wells are exposed to media alone, 2 $\mu$g/mL concanavalin A, 5 and 25 $\mu$g/mL Mab H221, and 5:1 or 25:1 (splenocyte: stimulator) mitomycin C killed H221 hybridoma cells. $10^6$ hybridoma cells/mL were treated with 25 $\mu$g/mL mitomycin C for 45 minutes at 37° C. in PBS then washed three times with PBS to remove toxin. After three days of culture at 37° C. with 5% $CO_2$, 1 $\mu$Ci tritiated thymidine (NEN Life Sciences, Boston Mass.) is added in 20 $\mu$L media and 18 hours later the plates are harvested on the Tomtec Harvester 96 (Tomtec, Orange, Conn.). Filtermats are dried and then counted with Beta scint on the Microbeta 1450 scintillation counter (Wallac Inc., Gaithersburg, Md.).

Cytotoxic T Cell Assay

Splenocytes are cultured at $5 \times 10^5$/mL with 2 $\mu$g/mL concanavalin A and mitomycin C treated stimulators at 20:1 splenocyte to stimulator ratio for 24 hours at which point the media is changed to remove the mitogen. After an additional four days of culture the cells are collected into 10 mL of media and centrifuged over Ficoll for 20 minutes at 1500 g. Cells were then counted and plated at 100:1, 50:1, 25:1 and 12.5:1 effector: target with a constant number of target cells in each round bottomed well. The target cells are prepared by resuspending $10^7$ viable H221 cells in 250 $\mu$L media and adding 75 $\mu$Ci $^{51}$Cr-sodium chromate (NEN/Life Sciences Inc., Boston, Mass.) and incubating for 2 hours at room temperature. These cells were then washed 3 times with RPMI complete media and resuspended for plating. Plates were centrifuged at 800 rpm for 2 minutes and then incubated at 37° C. for 5 and 16 hours at which times 50 $\mu$L of the supernatant was carefully removed and counted with Optiphase scintillation fluid (Wallace Inc., Gaithersburg, Md.) in the scintillation counter. Percent specific lysis was calculated as per the following equation:

$$\% \text{ specific lysis} = \frac{\text{Experimental Release} - \text{Spontaneous Release}}{\text{Total Release} - \text{Spontaneous Release}}$$

(Spontaneous release are those cpm released from cells incubated in media alone and total release are those released by total lysis of target cells by incubation in 1% SDS.)

In Vivo Tumor Challenge

Mice were primed with pristane (1 mL intraperitoneally) at the time of the last of 3 DNA inoculations. One week later the mice (6 per group) were injected intraperitoneally with $10^6$ viable H221 hybridoma cells which had been washed twice and resuspended in sterile PBS at $10^7$/mL. Mice were checked weekly for the first two weeks and then twice weekly thereafter for signs of tumor growth (palpable masses and/or ascites). At 4 weeks following challenge, the mice were sacrificed, solid tumors were dissected and weighed to quantify tumor mass. In mice with malignant ascites, the cellular content of ascites was also weighed and added to the tumor mass.

Anti-DNA Antibody Assay

Sera from mice were tested in an anti-dsDNA ELISA (Madaio, et al. 1984 J. Immunol. 132:872, which is incorporated herein by reference).

Results

Idiotypic DNA Inoculation Elicits Specific Immune Responses

In preliminary experiments, purified plasmid DNA was inoculated into AKR×DBA/2 mice, and following several boosts the mice were evaluated for cellular and humoral immune responses. Controls included killed hybridoma cells and purified H221 mAb. Both lymphocyte proliferative and cytotoxic T cell responses were elicited against H221 cells with the constructs in the absence of a detectable serologic response against anti-DNA IL/IM Fab fragments (detection was with labeled Streptococcal protein G). The cellular immune responses were evaluated more closely. Groups of four AKR×DBA/2 mice were inoculated once with plasmid DNA with bupivacaine-HCl simultaneously. One week later, they were sacrificed and evaluated for cytotoxic T cell and proliferative responses. The results are shown in FIGS. 9 and 10.

In the experiments to evaluate the proliferative response of spleenocytes following a single DNA inoculation, mice were inoculated once with 100 µg plasmid DNA in 0.25%. Bupivacaine, and one week later, the spleenocytes were removed and incubated either in media alone, with killed H221 cells or with H221 Fab. Proliferation was evaluated by stimulating the immune spleenocytes with either purified H221 mAb (25 or 5 µg/well) or with killed anti-DNA IL/IM hybridoma cells (20,000 or 100,000/well). The positive control was inoculation with killed H221 cells (killed cells), with the negative control inoculation with vector only. Following a 3 day culture, the cells were pulsed overnight with tritiated thymidine, and counts per minute (CPM) incorporated determined. The mean ACPM (experimental minus media only)± the standard deviation of triplicate wells is shown for two concentrations of Fab and two concentrations of killed H221 cells. The results are shown in FIG. 9.

Figure 10A:
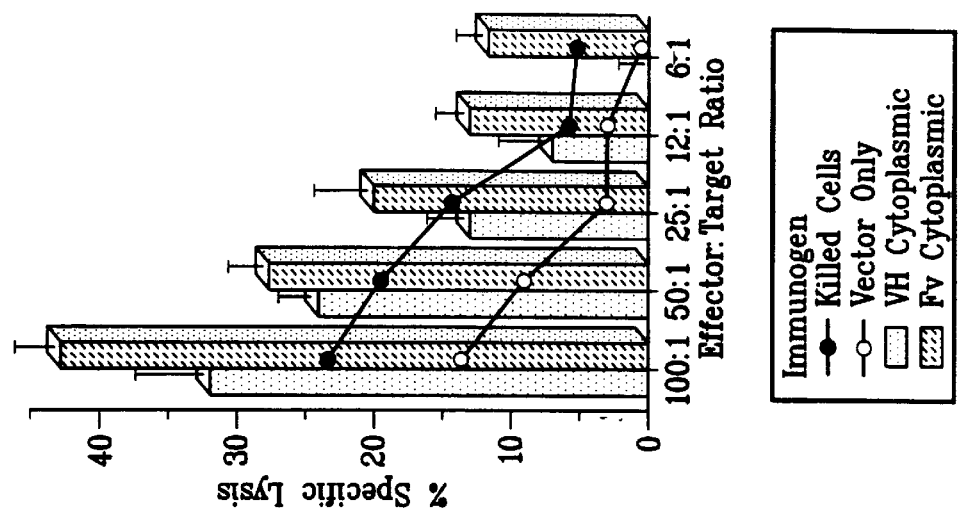
FIGS. 10A, 10B and 10C show results of experiments to evaluate the cytotoxic T cell (CTL) response following a single DNA inoculation.
Figure 10B:
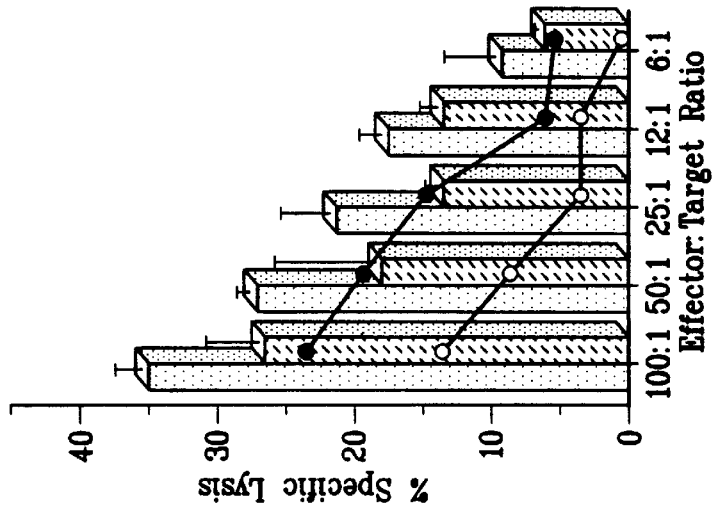
Figure 10C:
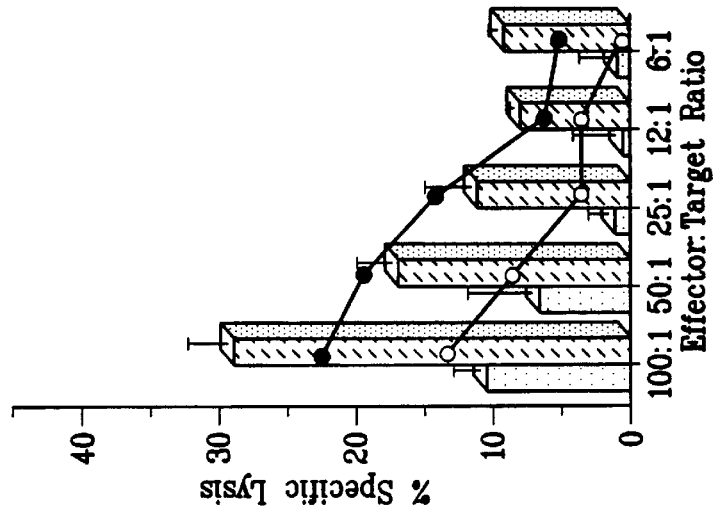

In the experiments to evaluate the cytotoxic T cell (CTL) response following a single DNA inoculation, mice were inoculated one with 100 µg plasmid DNA in 0.25% Bupivacaine, and one week later, the spleenocytes were removed and incubated with concanavalin A and killed H221 cells (20:1 effector:stimulator ration). After 24–48 hours the Con A was removed, the cells fed, and the culture continued for 5 days total. The positive control w as inoculation with killed H221 cells (killed cells), with the negative control inoculation with vector only. Following the 5 day culture, the effector cells were isolated by discontinuous gradient centrifugation, and used to lyse $^{51}$Cr labeled target cells at the various rations shown. % specific lysis was calculated as noted in Materials and Methods. The mean ± standard deviation % specific lysis is shown for triplicate determinations. The controls (killed H221 cells and vector only) are shown in all three graphs for reference. The results are shown in FIGS. 10A, 10B and 10C.

Figure 9:
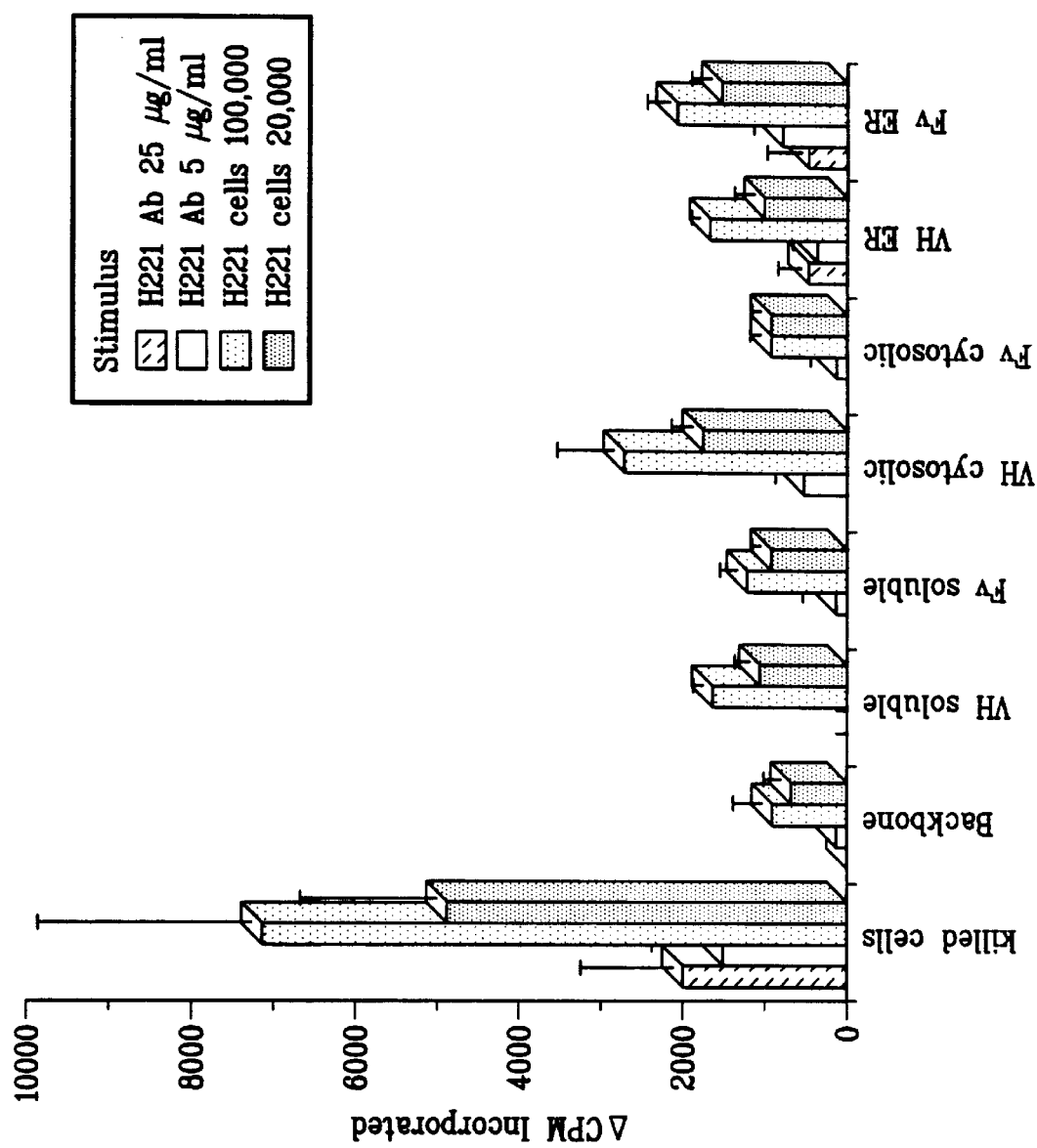
FIG. 9 shows results of experiments to evaluate the proliferative response of spleenocytes following a single DNA inoculation.

As in other experiments, the best proliferative responses were induced by the killed hybridoma cells (FIG. 9). Measurable responses (compared with vector only) were seen for most constructs, but were only modest in magnitude. The proliferative responses against purified mAb were significant (>2 standard errors above the backbone control) for the mice immunized with killed cells or with the ER-retained vaccines. The proliferative responses against the hybridoma cells were significant (>2 standard errors above the backbone control) for both ER-retained vaccines, and the $V_H$-soluble and $V_H$ cytosolic vaccines.

In contrast, the CTL responses elicited were striking (FIG. 10). All of the constructs except the soluble heavy chain V region ($V_H$ sol) elicited CTL activity as good or better than killed cells, which was the positive control for the assay. In other experiments, $V_H$ sol elicited significant CTL responses compared with controls (22% compared with 10% specific lysis at 100:1 effector: target ratio for the VH sol construct versus control in a typical experiment). Exceptional responses were seen for the cytosolic and ER targeted constructs indicating that targeting to these compartments boots the CTL responses. The Fv constructs generally elicited more potent CTLs, with the exception of the ER-retained vaccines.

Protection from Hybridoma Challenge

Figures 11A, 11B:
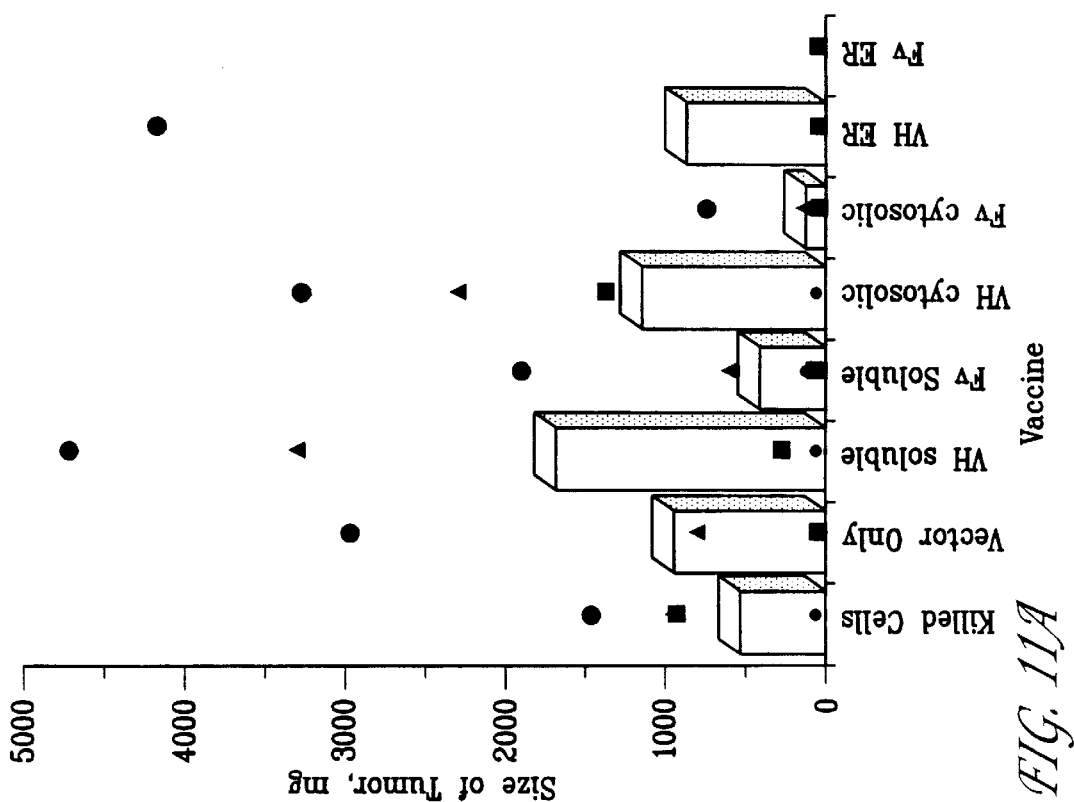
FIGS. 11A and 11B show data regarding survival and tumor burden following DNA inoculation and challenge.

To evaluate the efficacy of these DNA vaccines in protecting from challenge with autoantibody-producing hybridoma cells in vivo, groups of 5–6 mice were immunized three times at biweekly intervals with 100 µg of the DNA vaccines in bupivacaine. The mice were challenged with live anti-DNA LK/IM hybridoma cells (H221 cells) intraperitoneally. Four weeks letter, the mice were evaluated for tumor burden and ascites. All mice with tumors or ascites were sacrificed, tumors excised and Tumor burden determined. The results are shown in FIGS. 11A and 11B. FIG. 11A shows the tumor mass for each vaccinated group. The mean value is shown in a bar graph, with the values for individual mice superimposed. FIG. 11B shows the proportion of mice at 4 weeks developing tumors within each group is shown. Several of the DNA vaccines showed specific effects, as evidenced by reduced mean tumor burden. Both the $F_V$ AND $V_H$ ER retained vaccines prevented tumor formation in 6/6 and 4/5 miche respectively, compared with 3/6 immunized with killed cells and 2/5 receiving the vector control.

Nearly all of the mice evaluated demonstrated an increase in serum anti-DNA titers compared with baseline responses, although this was relatively small. There were no marked differences between groups in this parameter, although lower anti-DNA levels were seen in the group immunized with the Fv ER-retained vaccine compared with the vector only controls (a titer increase of 0.83±0.41 for the Fv ER-retained vaccines compared with 1.6±0.55 in the vector control mice, p=0.025 Student's t-Test). Thus, the most potent vaccine did significantly lower circulating anti-DNA levels in this model as well.

Immune Responses in Survivors

Figure 12:
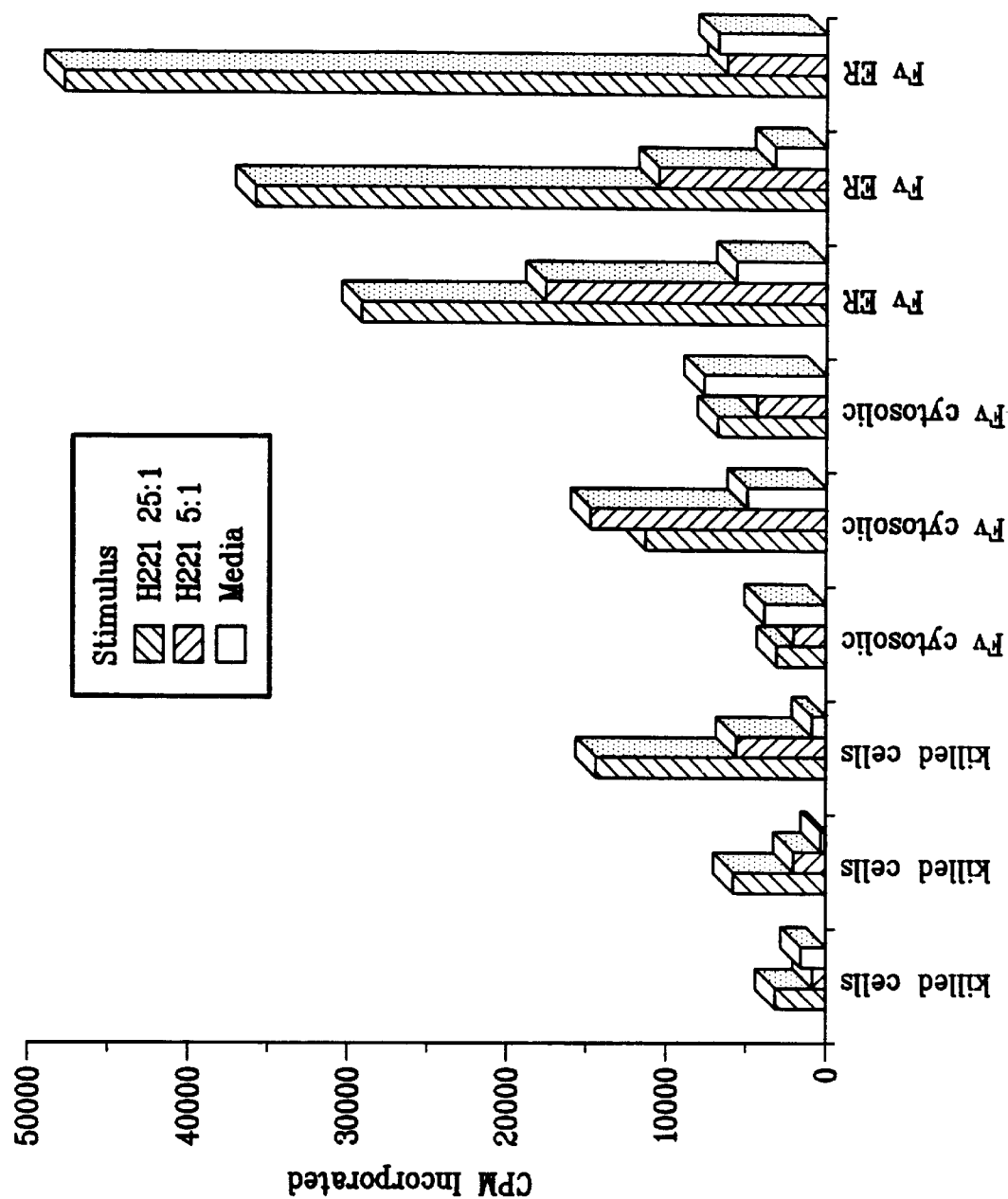
FIG. 12 shows data form experiments evaluating the proliferative response in survivors of tumor challenge.

CTL activity and proliferation in response to killed H221 cells in several mice that survived tumor challenge were evaluated. This included 3 mice immunized with killed cells, 3 mice immunized with the cytosolic Fv construct, and 3 mice immunized with the ER-retained Fv construct. The mice were sacrificed at week 5 (38 days following the initial tumor challenge) and proliferation of spleenocytes in response to killed H221 cells determined as described in FIG. 9. The mean CPM incorporated of triplicate wells is shown for individual mice, labeled according to the vaccine they received. The CTL responses had waned (the mice had not been boosted prior to the assay) with the highest response (13% specific lysis at a 50:1 effector:target ratio) seen in the mice immunized with the ER retained construct, but with similar responses seen in the other (7% in the killed cells immunized and 7% in the Fv cytosolic construct immunized mice). In contrast, the proliferative responses were still vigorous (FIG. 12). Mice initially immunized with killed cells or the cytosolic targeted Fv construct responded to killed H221 cells in vitro (mean values of 7,488±5,864 CPM dn 6,663±4,171 CPM respectively, compared with 721±409 and 5,044±1902 for media alone controls). In contrast, those mice initially immunized with the ER retained Fv construct responded to killed H221 cells in vitro (mean 37,351±9,004 CPM versus 4,651±1,345 with media alone). This exuberant proliferative response was mirrored by enhanced IL-2 production in parallel cultures (on the average, there was twice as high in the Fv ER-retained vaccines compared with those immunized with killed cells). Together, these results indicate a strong cellular proliferative response in the mice immunized with the Fv ER-retained vaccine who survived challenge.

Discussion

These studies indicate that idiotypic DNA vaccination is capable of eliciting a cellular immune response in the absence of a detectable humoral immune response. Furthermore, for most of the vaccines evaluated the CTL response was equivalent to or surpassed the CTL response elicited by killed cells (FIG. 10). In contrast to the killed cell vaccine, however, the proliferative response (which typically correlates with $T_H$ responses) was barely detectable following DNA vaccination (FIG. 9). Thus, it is possible with idiotypic DNA vaccination to elicit a potent CTL response with only a slight $T_H$ response. This allows investigation of the efficacy of CTL's in inducing protective immunity. The immunogenicity of these idiotypic DNA vaccines was markedly enhanced by targeting the DNA vaccine to specific intracellular compartments, particularly with regard to CTL responses (FIG. 10). Targeting to the cytosol and retention in the ER enhanced the CTL responses, as would be expected for MHC class I restricted responses. The Fv vaccines ($V_H$ and $V_L$ regions together) were observed to be more immunogenic than the $V_H$ region alone. This is likely due to the greater number of epitopes presented to the immune system. A direct effect of the linker peptide can not be ruled out.

Idiotypic DNA vaccination is capable of protecting mice from histocompatible tumor challenge if the vaccine is targeted to the appropriate intracellular compartment (FIG. 11). This protective response is clearly due to cellular immunity, as humoral immunity was not detectable in this system even in survivors from tumor challenge. The protection seen most likely was due to the CTL responses elicited, as a potent CTL response was elicited by the ER-retained vaccines, which were the "most protective" vaccines. This suggests that concentration of the antigen in the ER and elicitation of CTL's results in protective immunity. Other factors could be contributing to the protective responses such as the presence of non-self antigenic determinants in the constructs used for vaccination. The mice immunized with the ER-retained vaccine who survived tumor challenge mounted an impressive proliferative response (FIG. 12). This indicates that the ER-retained Fv DNA vaccine primed the immune system for a secondary response to the tumor challenge with marked expansion of idiotype-specific T cells. This proliferative response was not as high in the survivors who were initially immunized with the killed cells or the Fv cytosolic vaccine. This may relate to the timing of the immune response following challenge, as only a single time point was sampled in this study. However, a selective effect of the ER-retained vaccine in priming for a potent secondary response is supported by the complete protection from tumor challenge in this group.

The ability to manipulate the expression, cellular localization, and other parameters of DNA vaccines renders them particularly suited for investigations into the nature of induced immune responses which can lead to protection in vivo. DNA-vaccination has been used against a variety of model tumor antigens, including our studies using murine lymphoma cells expressing human CD4, a similar system using the beta-galactosidase gene, human carcinoembryonic antigen, a single epitope from a mutant form of the human p53 gene. These studies establish the utility of DNA vaccination against model tumor antigens. All of the antigens used were in fact foreign proteins which typically are much more immunogenic than tumor self-antigens which would be encountered clinically.

The use of the $V_H$ and $V_L$ regions of a murine lymphoma in an expression vector also encoding the human Cγ1 and $C_\kappa$ with or without linked expression of human GM-CSF has been reported (Syrengelas, et al. 1996 Nature Medicine 2:1038–1041, which is incorporated herein by reference). The immunogen thus had foreign antigenic determinants linked to the self-V regions of interest. Intramuscular or intradermal DNA inoculation with these constructs resulted in an anti-idiotypic antibody response, as well as partial protection from tumor challenge in vivo. The linked expression of human GM-CSF markedly enhanced the responses elicited. DNA immunization induced immune responses against a weak, otherwise unrecognized tumor antigen, this was dependent on additional stimuli with the DNA (i.e. the human constant regions and GM-CSF).

Isolated syngeneic V region DNA immunization has been shown to be capable of eliciting protective immune responses in a murine model of autoimmune disease. DNA based immunization against the murine Vβ8.2 gene has been shown to protect H-2$^u$ mice from experimental autoimmune encephalomyelitis (EAE) (Waisman, et al. 1996 Nature Medicine 2:899–905, which is incorporated herein by reference). Cellular immune responses were demonstrated, and that data suggested that the DNA immunization had shut off the pathogenic T cells, which are dominated by clones expressing Vβ8.2 in this system. No evidence of deletion of Vβ8.2-bearing cells with their vaccination approach (which used an isolated V region without associated a leader peptide or the CDR3) was shown.

TABLE 1

| | |
|---|---|
| Picornavirus Family Genera: | Rhinoviruses: |
| | (Medical) responsible for ~50% cases of the common cold. Etheroviruses: |
| | (Medical) includes polioviruses, coxsackieviruses, echoviruses, and human enteroviruses such as hepatitis A virus. Apthoviruses: |
| | (Veterinary) these are the foot and mouth disease viruses. |
| Target antigens: | VP1, VP2, VP3, VP4, VPG |
| Calcivirus Family Genera: | Norwalk Group of Viruses: |
| | (Medical) these viruses are an important causative agent of epidemic gastroenteritis. |

TABLE 1-continued

| | |
|---|---|
| Togavirus Family Genera: | Alphaviruses: |
| | (Medical and Veterinary) examples include Senilis viruses, RossRiver virus and Eastern & Western Equine encephalitis. |
| | Reovirus: |
| | (Medical) Rubella virus. |
| Flariviridue Family | Examples include: |
| | (Medical) dengue, yellow fever, Japanese encephalitis, St. Louis encephalitis and tick borne encephalitis viruses. |
| Hepatitis C Virus: | (Medical) these viruses are not placed in a family yet but are believed to be either a togavirus or a flavivirus. Most similarity is with togavirus family. |
| Coronavirus Family: | (Medical and Veterinary) Infectious bronchitis virus (poultry) Porcine transmissible gastroenteric virus (pig) Porcine hemagglutinating encephalomyelitis virus (pig) Feline infectious peritonitis virus (cats) Feline enteric coronavirus (cat) Canine coronavirus (dog) The human respiratory coronaviruses cause ~40 cases of common cold. EX. 224E, 0C43 Note - coronaviruses may cause non-A, B or C hepatitis |
| Target antigens: | E1 - also called M or matrix protein E2 - also called S or Spike protein E3 - also called HE or hemagglutin-elterose glycoprotein (not present in all coronaviruses) N - nucleocapsid |
| Rhabdovirus Family Genera: | Vesiliovirus Lyssavirus: |
| | (medical and veterinary) rabies |
| Target antigen: | G protein N protein |
| Filoviridue Family: | (Medical) Hemorrhagic fever viruses such as Marburg and Ebola virus |
| Paramxyovirus Family: Genera: | Paramyxovirus: |
| | (Medical and Veterinary) Mumps virus, New Castle disease virus (important pathogen in chickens) Morbillivirus: |
| | (Medical and Veterinary) Measles, canine distemper Pneuminivirus: |
| | (Medical and Veterinary) Respiratory syncytial virus |
| Orthomyxovirus Family | (Medical) The Influenza virus |
| Bungavirus Family Genera: | Bungavirus: |
| | (Medical) California encephalitis, LA Crosse Phlebovirus: |
| | (Medical) Rift Valley Fever |

TABLE 1-continued

| | |
|---|---|
| | Hantavirus: |
| | Puremala is a hemahagin fever virus Nairvirus (Veterinary) Nairobi sheep disease Also many unassigned bungaviruses (Medical) |
| Arenavirus Family | LCM, Lassa fever virus |
| Reovirus Family Genera: | Reovirus: |
| | a possible human pathogen |
| | Rotavirus: |
| | acute gastroenteritis in children |
| | Orbiviruses: |
| | (Medical and Veterinary) Colorado Tick fever, Lebombo (humans) equine encephalosis, blue tongue |
| Retrovirus Family Sub-Family: | Oncorivirinal: |
| | (Veterinary) (Medical) feline leukemia virus, HTLVI and HTLVII |
| | Lentivirinal: |
| | (Medical and Veterinary) HIV, feline immunodeficiency virus, equine infections, anemia virus Spumavirinal |
| Papovavirus Family Sub-Family: | Polyomaviruses: |
| | (Medical) BKU and JCU viruses |
| Sub-Family: | Papillomavirus: |
| | (Medical) many viral types associated with cancers or malignant progression of papilloma |
| Adenovirus | (Medical) EX AD7, ARD., O.B. - cause respiratory disease - some adenoviruses such as 275 cause enteritis |
| Parvovirus Family | (Veterinary) Feline parvovirus: |
| | causes feline enteritis Feline panleucopeniavirus Canine parvovirus Porcine parvovirus |
| Herpesvirus Family Sub-Family: Genera: | alphaherpesviridue Simplexvirus (Medical) HSVI, HSVII Varicellovirus: |
| | (Medical - Veterinary) pseudorabies - varicella zoster |
| Sub-Family - Genera: | betaherpesviridue Cytomegalovirus (Medical) HCMV Muromegalovirus |
| Sub-Family: Genera: | Gammaherpesviridue Lymphocryptovirus (Medical) EBV - (Burkitts lympho) Rhadinovirus |
| Poxvirus Family Sub-Family: | Chordopoxviridue (Medical - Veterinary) |
| Genera: | Variola (Smallpox) Vaccinia (Cowpox) Parapoxivirus - Veterinary Auipoxvirus - Veterinary Capripoxvirus Leporipoxvirus |

TABLE 1-continued

| | |
|---|---|
| Sub-Family: | Suipoxvirus<br>Entemopoxviridue |
| Hepadnavirus Family | Hepatitis B virus |
| Unclassified | Hepatitis delta virus |

TABLE 2

Bacterial pathogens

Pathogenic gram-positive cocci include: pneumococcal; staphylococcal; and streptococcal.
Pathogenic gram-negative cocci include: meningococcal; and gonococcal.
Pathogenic enteric gram-negative bacilli include: enterobacteriaceae; pseudomonas, acinetobacteria and eikenella; melioidosis; salmonella; shigellosis; hemophilus; chancroid; brucellosis; tularemia; yersinia (pasteurella); streptobacillus moniliformis and spirillum ; listeria monocytogenes; erysipelothrix rhusiopathiae; diphtheria; cholera; anthrax; donovanosis (granuloma inguinale); and bartonellosis.
Pathogenic anaerobic bacteria include: tetanus; botulism; other clostridia; tuberculosis; leprosy; and other mycobacteria. Pathogenic spirochetal diseases include: syphilis; treponematoses: yaws, pinta and endemic syphilis; and leptospirosis.

TABLE 2-continued

Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis.
Rickettsial infections include rickettsial and rickettsioses.
Examples of mycoplasma and chlamydial infections include: mycoplasma pneumoniae; lymphogranuloma venereum; psittacosis; and perinatal chlamydial infections.

Pathogenic eukaryotes

Pathogenic protozoans and helminths and infections thereby include: amebiasis; malaria; leishmaniasis; trypanosomiasis; toxoplasmosis; pneumocystis carinii; babesiosis; giardiasis; trichinosis; filariasis; schistosomiasis; nematodes; trematodes or flukes; and cestode (tapeworm) infections.

TABLE 3

Primers used for PCR and recombinant PCR

Secretory and ER-retained Leaders:

5' GGGCGGCCGC AATGGACATG AGGGTCCCCG CTCAGCTCCT GGGGCTCCTG (SEQ ID NO:8)

3' CCTCTAGAAC ATTTGGCACC TGGGAGCCAG AGCAGCAGGA GCCCCAGGAG C (SEQ ID NO:9)

Cytoplasmic Leader:

5' GGGCGGCCGC AATGGGATGG AGCTGTAAGA GGCGCTCCTC GGAAG (SEQ ID NO:10)

3' CCCTCTAGAG TGGACACCAG CTGTAGCTGT TTCTTCCGAG GAGCG (SEQ ID NO:11)

CD4 Transmembrane:

5' GTGCAGCCCA TGGCCCTGAT TGTG (SEQ ID NO:12)

3' TTCATTGGGC TAGGCATCTT CTTCAGATCT AGGTGC (SEQ ID NO:13)

ER-retention signal (adenovirus E19):

5' TTCTTCAGAT CTAGGCGCAG TTTTATTGAT GAA (SEQ ID NO:14)

3' CGTAAAACGC GTTTAAGGCA TTTTCTTTTC (SEQ ID NO:15)

5' Vkappa for Fv expression:

GGGGTTCTAG AGACATTGTG ATATCMCARW CTC (SEQ ID NO:16)

3' CL Primer (Written antiparallel) for expression with linker peptide:

CTGATAAGAT TTAGATTCGG AGCCAGAACC GGAAGATTTA CCTTCTGCAG CATCAGCCCG (SEQ ID NO:17)

TABLE 3-continued
Primers used for PCR and recombinant PCR

5' VH2 primer for single chain expression:

GGGGTTCTAG AGAGGTCCAG CTGCARCARY CTGG (SEQ ID NO:18)

5' VH Primer for expression with linker peptide:

GGCTCCGAAT CTAAATCTTA TCAGGAGGTC CAGCTGCARC ARYCTGG (SEQ ID NO:19)

3' IgG2a CH1 for transmembrane/ER retention:

ATAGACCATG GGGGCTGTTG TTTTGGC (SEQ ID NO:20)

3' IgG2a CH1 for soluble secretion:

ATAGAACGCG TGTCAGGCTG TTGTTTTGGC (SEQ ID NO:21)

M = A or C
R = A or G
W = T or A
Y = T or C

TABLE 4

Immunoglobulin Leader (ER Targeting for Secretion or Retention):

Met asp met arg val pro ala gln leu leu gly leu leu leu leu trp leu pro gly ala lys cys ser arg (SEQ ID NO:22)

Cytosolic Leader:

Met gly trp ser cys lys arg arg ser ser glu glu thr ala thr ala gly val his ser arg (SEQ ID NO:23)

H221 VL Region:

Asp ile val ile ser gln ser pro ser thr leu ala val ser ala gly glu lys val thr met asn cys lys ser ser gln ser leu phe asn ser arg thr arg lys asn tyr leu ala trp phe gln gln lys pro gly gln ser pro lys leu leu ile tyr trp ala ser thr arg glu ser gly val pro asp arg phe thr gly ser gly ser gly thr asp phe thr leu thr ile ser ser val gln ala glu asp leu ala val tyr tyr cys lys gln ser tyr tyr leu arg thr phe gly gly gly thr arg leu glu (SEQ ID NO:24)

Linker Peptide:

Arg ala asp ala ala glu gly lys ser ser gly ser gly ser glu ser lys ser tyr gln gly ser glu ser lys ser tyr gln (SEQ ID NO:25)

H221 VH Region:

Glu val gln leu gln gln ser gly ala glu leu val lys ser gly ala ser val lys leu ser cys lys ala ser gly phe thr phe thr ser tyr trp ile asn trp val lys gln arg ala gly gln gly leu glu trp ile gly asn ile tyr pro gly ser asn thr ile asn tyr ser glu asn phe lys lys lys ala thr leu thr val asp thr ser ser ser thr ala tyr met gln leu ser ser leu thr ser asp asp ser ala val tyr tyr cys ala arg glu arg leu leu gly phe val tyr trp gly gln gly thr leu val thr val ser thr ala lys thr thr ala (SEQ ID NO:26)

TABLE 4-continued

CD4 transmembrane and E19 cytoplasmic Domains (for ER retention):

Met ala leu ile val leu gly gly val ala gly leu leu leu phe ile gly leu gly ile phe phe arg ser arg arg ser phe ile asp glu lys lys met pro (SEQ ID NO:27)

What is claimed is:

1. A plasmid comprising a nucleotide sequence that encodes an immunogenic target protein linked to or comprising an intracellular targeting sequence, operably linked to regulatory elements, wherein said intracellular targeting sequence is DKQTLL (SEQ ID NO:1) or DEKKMP (SEQ ID NO:3) at the C terminal of said immunogenic target protein.

2. A plasmid comprising a nucleotide sequence encoding an immunogenic target protein linked to or comprising an intracellular targeting sequence, operably linked to regulatory elements, wherein said intracellular targeting sequence directs said immunogenic target protein to be secreted.

3. The plasmid of claim 2 wherein said immunogenic target protein is an allergen, pathogen antigen, cancer-associated antigen or antigen linked to cells associated with autoimmune diseases, or can induce an immune response that cross-reacts with an allergen, pathogen antigen, cancer-associated antigen or antigen linked to cells associated with autoimmune diseases.

4. The plasmid of claim 2 wherein said immunogenic target protein is an allergen, pathogen antigen, cancer-associated antigen or antigen linked to cells associated with autoimmune diseases.

5. The plasmid of claim 2 wherein said intracellular targeting sequence is an N-terminal hydrophobic leader sequence or an immunoglobulin leader sequence.

6. The plasmid of claim 2 wherein said intracellular targeting sequence comprises SEQ ID NO:22.

7. A pharmaceutical composition comprising the plasmid of claim 2.

8. The pharmaceutical composition of claim 7 further comprising a polynucleotide function enhancer.

9. The pharmaceutical composition of claim 8 wherein said polynucleotide function enhancer is bupivacaine.

10. A method of immunizing an individual against an antigen comprising administering to said individual the plasmid of claim 2.

11. A plasmid comprising a nucleotide sequence encoding an immunogenic target protein linked to or comprising an intracellular targeting sequence, operably linked to regulatory elements, wherein said intracellular targeting sequence directs said immunogenic target protein to be localized in the cytoplasm of a cell.

12. The plasmid of claim 11 wherein said immunogenic target protein is an allergen, pathogen antigen, cancer-associated antigen or antigen linked to cells associated with autoimmune diseases, or can induce an immune response that cross-reacts with an allergen, pathogen antigen, cancer-associated antigen or antigen linked to cells associated with autoimmune diseases.

13. The plasmid of claim 11 wherein said immunogenic target protein is an allergen, pathogen antigen, cancer-associated antigen or antigen linked to cells associated with autoimmune diseases.

14. The plasmid of claim 11 wherein said intracellular targeting sequence comprises SEQ ID NO:23.

15. A pharmaceutical composition comprising the plasmid of claim 11.

16. The pharmaceutical composition of claim 15 further comprising a polynucleotide function enhancer.

17. The pharmaceutical composition of claim 16 wherein said polynucleotide function enhancer is bupivacaine.

18. A method of immunizing an individual against an antigen comprising administering to said individual the plasmid of claim 11.

19. A plasmid comprising a nucleotide sequence encoding an immunogenic target protein linked to or comprising an intracellular targeting sequence, operably linked to regulatory elements, wherein said intracellular targeting sequence directs said immunogenic target protein to be localized in the cell membrane of a cell.

20. The plasmid of claim 19 wherein said immunogenic target protein is an allergen, pathogen antigen, cancer-associated antigen or antigen linked to cells associated with autoimmune diseases, or can induce an immune response that cross-reacts with an allergen, pathogen antigen, cancer-associated antigen or antigen linked to cells associated with autoimmune diseases.

21. The plasmid of claim 19 wherein said immunogenic target protein is an allergen, pathogen antigen, cancer-associated antigen or antigen linked to cells associated with autoimmune diseases.

22. The plasmid of claim 19 wherein said intracellular targeting sequence comprises an N-terminal hydrophobic sequence and an internal hydrophobic region.

23. A pharmaceutical composition comprising the plasmid of claim 19.

24. The pharmaceutical composition of claim 23 further comprising a polynucleotide function enhancer.

25. The pharmaceutical composition of claim 24 wherein said polynucleotide function enhancer is bupivacaine.

26. A method of immunizing an individual against an antigen comprising administering to said individual the plasmid of claim 19.

27. A plasmid comprising a nucleotide sequence encoding an immunogenic target protein linked to or comprising an intracellular targeting sequence, operably linked to regulatory elements, wherein said intracellular targeting sequence directs said immunogenic target protein to be localized in the endoplasmic reticulum of a cell, and wherein said immunogenic target protein is an allergen, pathogen antigen, cancer-associated antigen or antigen linked to cells associated with autoimmune diseases, or can induce an immune response that cross-reacts with an allergen, pathogen antigen, cancer-associated antigen or antigen linked to cells associated with autoimmune diseases.

28. The plasmid of claim 27 wherein said immunogenic target protein is an allergen, pathogen antigen, cancer-associated antigen or antigen linked to cells associated with autoimmune diseases.

29. The plasmid of claim 27 wherein said intracellular targeting sequence comprises SEQ ID NO:3 at the C-terminus of said immunogenic target protein or SEQ ID NO:27.

30. A pharmaceutical composition comprising the plasmid of claim 27.

31. The pharmaceutical composition of claim 30 further comprising a polynucleotide function enhancer.

32. The pharmaceutical composition of claim 31 wherein said polynucleotide function enhancer is bupivacaine.

33. A method of immunizing an individual against an antigen comprising administering to said individual the plasmid of claim 27.

34. A plasmid comprising a nucleotide sequence encoding an immunogenic target protein linked to or comprising an intracellular targeting sequence, operably linked to regulatory elements, wherein said intracellular targeting sequence directs said immunogenic target protein to be localized in a lysosome of a cell, and wherein said intracellular targeting sequence comprises SEQ ID NO:1.

35. The plasmid of claim 34 wherein said immunogenic target protein is an allergen, pathogen antigen, cancer-associated antigen or antigen linked to cells associated with autoimmune diseases, or can induce an immune response that cross-reacts with an allergen, pathogen antigen, cancer-associated antigen or antigen linked to cells associated with autoimmune diseases.

36. The plasmid of claim 35 wherein said immunogenic target protein is an allergen, pathogen antigen, cancer-associated antigen or antigen linked to cells associated with autoimmune diseases.

37. A pharmaceutical composition comprising the plasmid of claim 34.

38. The pharmaceutical composition of claim 37 further comprising a polynucleotide function enhancer.

39. The pharmaceutical composition of claim 38 wherein said polynucleotide function enhancer is bupivacaine.

40. A method of immunizing an individual against an antigen comprising administering to said individual the plasmid of claim 34.

* * * * *

UNITED STATES PATENT AND TRADEMARK OFFICE
CERTIFICATE OF CORRECTION

PATENT NO.    : 6,228,621 B1                                    Page 1 of 1
DATED         : May 8, 2001
INVENTOR(S)   : William V. Williams et al.

It is certified that error appears in the above-identified patent and that said Letters Patent is hereby corrected as shown below:

Column 19,
Line 17, after "responses" the next sentence should follow.

Signed and Sealed this

Sixteenth Day of April, 2002

Attest:

JAMES E. ROGAN
Attesting Officer    Director of the United States Patent and Trademark Office

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 6 amino acids
      (B) TYPE: amino acid
      (D) TOPOLOGY: both (ii) MOLECULE TYPE: peptide (xi) SEQUENCE DESCRIPTION: SEQ ID NO:1:

Asp Lys Gln Thr Leu Leu
1               5

(2) INFORMATION FOR SEQ ID NO:2:

(i) SEQUENCE CHARACTERISTICS:
      (A) LENGTH: 4 amino acids
      (B) TYPE: amino acid
      (D) TOPOLOGY: both (ii) MOLECULE TYPE: peptide (xi) SEQUENCE DESCRIPTION: SEQ ID NO:2:

Lys Asp Glu Leu
1

(2) INFORMATION FOR SEQ ID NO:3:

(i) SEQUENCE CHARACTERISTICS:
      (A) LENGTH: 6 amino acids
      (B) TYPE: amino acid
      (D) TOPOLOGY: both (ii) MOLECULE TYPE: peptide (xi) SEQUENCE DESCRIPTION: SEQ ID NO:3:

Asp Glu Lys Lys Met Pro
1               5

(2) INFORMATION FOR SEQ ID NO:4:

(i) SEQUENCE CHARACTERISTICS:
      (A) LENGTH: 330 base pairs
      (B) TYPE: nucleic acid
      (C) STRANDEDNESS: both
      (D) TOPOLOGY: both (ii) MOLECULE TYPE: cDNA (ix) FEATURE:
      (A) NAME/KEY: CDS
      (B) LOCATION: 1..330

(xi) SEQUENCE DESCRIPTION: SEQ ID NO:4:

```
GAC ATT GTG ATA TCA CAG TCT CCA TCC ACC CTG GCT GTG TCA GCA GGA        48
Asp Ile Val Ile Ser Gln Ser Pro Ser Thr Leu Ala Val Ser Ala Gly
 1               5                  10                  15

GAG AAG GTC ACT ATG AAC TGC AAA TCC AGT CAG AGT CTG TTC AAC AGT        96
Glu Lys Val Thr Met Asn Cys Lys Ser Ser Gln Ser Leu Phe Asn Ser
             20                  25                  30

AGA ACC CGA AAG AAC TAC TTG GCT TGG TTC CAG CAG AAA CCA GGG CAG       144
Arg Thr Arg Lys Asn Tyr Leu Ala Trp Phe Gln Gln Lys Pro Gly Gln
         35                  40                  45

TCT CCT AAA CTG CTG ATC TAC TGG GCA TCC ACT AGG GAA TCT GGG GTC       192
Ser Pro Lys Leu Leu Ile Tyr Trp Ala Ser Thr Arg Glu Ser Gly Val
     50                  55                  60

CCT GAT CGC TTC ACA GGC AGT GGA TCT GGG ACA GAT TTC ACT CTC ACC       240
Pro Asp Arg Phe Thr Gly Ser Gly Ser Gly Thr Asp Phe Thr Leu Thr
 65                  70                  75                  80

ATC AGC AGT GTG CAG GCT GAA GAC CTG GCA GTT TAT TAC TGC AAG CAA       288
Ile Ser Ser Val Gln Ala Glu Asp Leu Ala Val Tyr Tyr Cys Lys Gln
                 85                  90                  95

TCT TAT TAT CTT CGG ACG TTC GGT GGA GGC ACC AGG CTG GAA               330
Ser Tyr Tyr Leu Arg Thr Phe Gly Gly Gly Thr Arg Leu Glu
             100                 105                 110
```

(2) INFORMATION FOR SEQ ID NO:5:

(i) SEQUENCE CHARACTERISTICS:
        (A) LENGTH: 110 amino acids
        (B) TYPE: amino acid
        (D) TOPOLOGY: both (ii) MOLECULE TYPE: peptide (xi) SEQUENCE DESCRIPTION: SEQ ID NO:5:

```
Asp Ile Val Ile Ser Gln Ser Pro Ser Thr Leu Ala Val Ser Ala Gly
 1               5                  10                  15

Glu Lys Val Thr Met Asn Cys Lys Ser Ser Gln Ser Leu Phe Asn Ser
             20                  25                  30

Arg Thr Arg Lys Asn Tyr Leu Ala Trp Phe Gln Gln Lys Pro Gly Gln
         35                  40                  45

Ser Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Tyr Leu Arg Thr Phe Gly Gly Gly Thr Arg Leu Glu
             100                 105                 110
```

(2) INFORMATION FOR SEQ ID NO:6:

(i) SEQUENCE CHARACTERISTICS:
        (A) LENGTH: 423 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..427

(xi) SEQUENCE DESCRIPTION: SEQ ID NO:6:

```
GAG GTC CAG CTG CAG CAG CCT GGT GCT GAA CTT GTG AAG TCT GGG GCC      48
Glu Val Gln Leu Gln Gln Pro Gly Ala Glu Leu Val Lys Ser Gly Ala
  1               5                  10                  15

TCA GTG AAG CTG TCC TGC AAG GCT TCT GAC TTC ACT TTC ACC AGC TAC      96
Ser Val Lys Leu Ser Cys Lys Ala Ser Asp Phe Thr Phe Thr Ser Tyr
             20                  25                  30

TGG ATA AAC TGG GTG AAA CAG AGG CCT GGA CAA GGC CTT GAG TGG ATT     144
Trp Ile Asn Trp Val Lys Gln Arg Pro Gly Gln Gly Leu Glu Trp Ile
         35                  40                  45

GGA AAA TTT TAT CCT GGT AGT GGT ACT ATT AAC TAC AGT GAA AAT TTT     192
Gly Lys Phe Tyr Pro Gly Ser Gly Thr Ile Asn Tyr Ser Glu Asn Phe
     50                  55                  60

AAG AAA AAG GCC ACA CTG ACT GTA GAC ACA TCC TCC AGT ACA TCC TAC     240
Lys Lys Lys Ala Thr Leu Thr Val Asp Thr Ser Ser Ser Thr Ser Tyr
 65                  70                  75                  80

ATG CAG CTC AGC AGC CTG ACA TCT GAC GAC TCT GCG GTC TAT TAT TGT     288
Met Gln Leu Ser Ser Leu Thr Ser Asp Asp Ser Ala Val Tyr Tyr Cys
                 85                  90                  95

GCA AGA GAA CGT CTC CTG GGG TTT GTT TAT TGG GGC CAA GGG ACT CTG     336
Ala Arg Glu Arg Leu Leu Gly Phe Val Tyr Trp Gly Gln Gly Thr Leu
                100                 105                 110

GTC ACT GTC TCT ACA GCC AAA ACA ACA GCC CCA TCG GTC TAT CGG GGA     384
Val Thr Val Ser Thr Ala Lys Thr Thr Ala Pro Ser Val Tyr Arg Gly
            115                 120                 125

TCC TCT AGA GTC GAC CTG CAG GCA TGC AAG CTT GGC ACT                 423
Ser Ser Arg Val Asp Leu Gln Ala Cys Lys Leu Gly Thr
        130                 135                 140
```

(2) INFORMATION FOR SEQ ID NO:7:

(i) SEQUENCE CHARACTERISTICS:
        (A) LENGTH: 141 amino acids
        (B) TYPE: amino acid
        (D) TOPOLOGY: both (ii) MOLECULE TYPE: peptide (xi) SEQUENCE DESCRIPTION: SEQ ID NO:7:

```
Glu Val Gln Leu Gln Gln Pro Gly Ala Glu Leu Val Lys Ser Gly Ala
  1               5                  10                  15

Ser Val Lys Leu Ser Cys Lys Ala Ser Asp Phe Thr Phe Thr Ser Tyr
             20                  25                  30

Trp Ile Asn Trp Val Lys Gln Arg Pro Gly Gln Gly Leu Glu Trp Ile
         35                  40                  45

Gly Lys Phe Tyr Pro Gly Ser Gly Thr Ile Asn Tyr Ser Glu Asn Phe
     50                  55                  60

Lys Lys Lys Ala Thr Leu Thr Val Asp Thr Ser Ser Ser Thr Ser Tyr
 65                  70                  75                  80

Met Gln Leu Ser Ser Leu Thr Ser Asp Asp Ser Ala Val Tyr Tyr Cys
                 85                  90                  95

Ala Arg Glu Arg Leu Leu Gly Phe Val Tyr Trp Gly Gln Gly Thr Leu
                100                 105                 110

Val Thr Val Ser Thr Ala Lys Thr Thr Ala Pro Ser Val Tyr Arg Gly
            115                 120                 125

Ser Ser Arg Val Asp Leu Gln Ala Cys Lys Leu Gly Thr
        130                 135                 140
```

(2) INFORMATION FOR SEQ ID NO:8:

(i) SEQUENCE CHARACTERISTICS:
    (A) LENGTH: 50 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO:8:

GGGCGGCCGC AATGGACATG AGGGTCCCCG CTCAGCTCCT GGGGCTCCTG           50

(2) INFORMATION FOR SEQ ID NO:9:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

CCTCTAGAAC ATTTGGCACC TGGGAGCCAG AGCAGCAGGA GCCCCAGGAG C         51

(2) INFORMATION FOR SEQ ID NO:10:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

GGGCGGCCGC AATGGGATGG AGCTGTAAGA GGCGCTCCTC GGAAG               45

(2) INFORMATION FOR SEQ ID NO:11:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CCCTCTAGAG TGGACACCAG CTGTAGCTGT TTCTTCCGAG GAGCG               45

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GTGCAGCCCA TGGCCCTGAT TGTG                                      24

(2) INFORMATION FOR SEQ ID NO:13:

(i) SEQUENCE CHARACTERISTICS:
        (A) LENGTH: 36 base pairs
        (B) TYPE: nucleic acid (C) STRANDEDNESS: single
          (D) TOPOLOGY: linear (ii) MOLECULE TYPE: DNA (xi) SEQUENCE DESCRIPTION: SEQ ID NO:13:

TTCATTGGGC TAGGCATCTT CTTCAGATCT AGGTGC                                   36

(2) INFORMATION FOR SEQ ID NO:14:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:14:

TTCTTCAGAT CTAGGCGCAG TTTTATTGAT GAA                                      33

(2) INFORMATION FOR SEQ ID NO:15:

(i) SEQUENCE CHARACTERISTICS:
          (A) LENGTH: 30 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:15:

CGTAAAACGC GTTTAAGGCA TTTTCTTTTC                                          30

(2) INFORMATION FOR SEQ ID NO:16:

(i) SEQUENCE CHARACTERISTICS:
          (A) LENGTH: 33 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:16:

GGGGTTCTAG AGACATTGTG ATATCMCARW CTC                                      33

(2) INFORMATION FOR SEQ ID NO:17:

(i) SEQUENCE CHARACTERISTICS:
          (A) LENGTH: 60 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:17:

CTGATAAGAT TTAGATTCGG AGCCAGAACC GGAAGATTTA CCTTCTGCAG CATCAGCCCG          60

(2) INFORMATION FOR SEQ ID NO:18:

(i) SEQUENCE CHARACTERISTICS:
          (A) LENGTH: 34 base pairs
          (B) TYPE: nucleic acid
          (C) STRANDEDNESS: single
          (D) TOPOLOGY: linear (ii) MOLECULE TYPE: DNA (xi) SEQUENCE DESCRIPTION: SEQ ID NO:18:

GGGGTTCTAG AGAGGTCCAG CTGCARCARY CTGG                                34

(2) INFORMATION FOR SEQ ID NO:19:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

GGCTCCGAAT CTAAATCTTA TCAGGAGGTC CAGCTGCARC ARYCTGG                  47

(2) INFORMATION FOR SEQ ID NO:20:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

ATAGACCATG GGGGCTGTTG TTTTGGC                                        27

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

ATAGAACGCG TGTCAGGCTG TTGTTTTGGC                                     30

(2) INFORMATION FOR SEQ ID NO:22:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:22:

Met Asp Met Arg Val Pro Ala Gln Leu Leu Gly Leu Leu Leu Leu Trp
 1               5                  10                  15
Leu Pro Gly Ala Lys Cys Ser Arg
            20

(2) INFORMATION FOR SEQ ID NO:23:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (xi) SEQUENCE DESCRIPTION: SEQ ID NO:23:

```
Met Gly Trp Ser Cys Lys Arg Arg Ser Ser Glu Glu Thr Ala Thr Ala
  1               5                  10                  15

Gly Val His Ser Arg
             20
```

(2) INFORMATION FOR SEQ ID NO:24:

(i) SEQUENCE CHARACTERISTICS:
        (A) LENGTH: 110 amino acids
        (B) TYPE: amino acid
        (D) TOPOLOGY: linear (ii) MOLECULE TYPE: peptide (xi) SEQUENCE DESCRIPTION: SEQ ID NO:24:

```
Asp Ile Val Ile Ser Gln Ser Pro Ser Thr Leu Ala Val Ser Ala Gly
  1               5                  10                  15

Glu Lys Val Thr Met Asn Cys Lys Ser Ser Gln Ser Leu Phe Asn Ser
             20                  25                  30

Arg Thr Arg Lys Asn Tyr Leu Ala Trp Phe Gln Gln Lys Pro Gly Gln
         35                  40                  45

Ser Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Tyr Leu Arg Thr Phe Gly Gly Gly Thr Arg Leu Glu
            100                 105                 110
```

(2) INFORMATION FOR SEQ ID NO:25:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:25:

```
Arg Ala Asp Ala Ala Glu Gly Lys Ser Ser Gly Ser Gly Ser Glu Ser
  1               5                  10                  15

Lys Ser Tyr Gln Gly Ser Glu Ser Lys Ser Tyr Gln
             20                  25
```

(2) INFORMATION FOR SEQ ID NO:26:

(i) SEQUENCE CHARACTERISTICS:
        (A) LENGTH: 122 amino acids
        (B) TYPE: amino acid
        (D) TOPOLOGY: linear (ii) MOLECULE TYPE: peptide (xi) SEQUENCE DESCRIPTION: SEQ ID NO:26:

```
Glu Val Gln Leu Gln Gln Ser Gly Ala Glu Leu Val Lys Ser Gly Ala
  1               5                  10                  15

Ser Val Lys Leu Ser Cys Lys Ala Ser Gly Phe Thr Phe Thr Ser Tyr
             20                  25                  30

Trp Ile Asn Trp Val Lys Gln Arg Ala Gly Gln Gly Leu Glu Trp Ile
         35                  40                  45
```

```
                               -continued

Gly Asn Ile Tyr Pro Gly Ser Asn Thr Ile Asn Tyr Ser Glu Asn Phe
         50                  55                  60

Lys Lys Lys Ala Thr Leu Thr Val Asp Thr Ser Ser Ser Thr Ala Tyr
 65                  70                  75                  80

Met Gln Leu Ser Ser Leu Thr Ser Asp Asp Ser Ala Val Tyr Tyr Cys
                     85                  90                  95

Ala Arg Glu Arg Leu Leu Gly Phe Val Tyr Trp Gly Gln Gly Thr Leu
                100                 105                 110

Val Thr Val Ser Thr Ala Lys Thr Thr Ala
                115                 120

(2) INFORMATION FOR SEQ ID NO:27:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (xi) SEQUENCE DESCRIPTION: SEQ ID NO:27:

Met Ala Leu Ile Val Leu Gly Gly Val Ala Gly Leu Leu Leu Phe Ile
 1               5                  10                  15

Gly Leu Gly Ile Phe Phe Arg Ser Arg Arg Ser Phe Ile Asp Glu Lys
                20                  25                  30

Lys Met Pro
         35
```